United States Patent
Dimock

(10) Patent No.: US 8,252,842 B2
(45) Date of Patent: Aug. 28, 2012

(54) POLYMORPHIC FORM OF N-(S)-(3,4-DIFLUORO-2-(2-FLUORO-4-IODO-PHENYLAMINO)-6-METHOXYPHENYL)-1-(2,3-DIHYDROXYPROPYL)CYCLOPROPANE-1-SULFONAMIDE AND USES THEREOF

(75) Inventor: Stuart Dimock, Lake Forest, CA (US)

(73) Assignee: Ardea Biosciences, Inc., San Diego, CA (US)

( * ) Notice: Subject to any disclaimer, the term of this patent is extended or adjusted under 35 U.S.C. 154(b) by 0 days.

(21) Appl. No.: 13/181,864

(22) Filed: Jul. 13, 2011

(65) Prior Publication Data

US 2012/0016034 A1   Jan. 19, 2012

Related U.S. Application Data

(62) Division of application No. 12/399,848, filed on Mar. 6, 2009, now Pat. No. 8,044,240.

(60) Provisional application No. 61/034,464, filed on Mar. 6, 2008.

(51) Int. Cl.
*A61K 31/18* (2006.01)
*C07C 311/14* (2006.01)

(52) U.S. Cl. ......................................... 514/601; 564/80

(58) Field of Classification Search ........................ None
See application file for complete search history.

(56) References Cited

U.S. PATENT DOCUMENTS

| 7,759,518 | B2 | 7/2010 | Maderna et al. |
| 7,820,664 | B2 | 10/2010 | Vernier et al. |
| 2008/0058340 | A1 | 3/2008 | Maderna et al. |
| 2009/0227681 | A1 | 9/2009 | Dimock |

FOREIGN PATENT DOCUMENTS

WO  WO 2007/121269 A2   10/2007

OTHER PUBLICATIONS

Search Report for related Taiwan Patent Application No. 098107166, issued on Mar. 22, 2012.

*Primary Examiner* — Brian J Davis
(74) *Attorney, Agent, or Firm* — Millen, White, Zelano & Branigan, P.C.

(57) ABSTRACT

Disclosed herein, in certain embodiments, is a crystalline polymorph form A of N—(S)-(3,4-difluoro-2-(2-fluoro-4-iodophenylamino)-6-methoxyphenyl)-1-(2,3-dihydroxypropyl)cyclopropane-1-sulfonamide. Further disclosed herein, in certain embodiments, are pharmaceutical compositions comprising the crystalline polymorph form A of N—(S)-(3,4-difluoro-2-(2-fluoro-4-iodophenylamino)-6-methoxyphenyl)-1-(2,3-dihydroxypropyl)cyclopropane-1-sulfonamide.

20 Claims, 5 Drawing Sheets

POLYMORPHIC FORM OF N-(S)-(3,4-DIFLUORO-2-(2-FLUORO-4-IODO-PHENYLAMINO)-6-METHOXYPHENYL)-1-(2,3-DIHYDROXYPROPYL)CYCLOPROPANE-1-SULFONAMIDE AND USES THEREOF

CROSS REFERENCE TO RELATED APPLICATIONS

This application is a divisional application of U.S. Ser. No. 12/399,848, filed Mar. 6, 2009, now U.S. Pat. No. 8,044,240, issued Oct. 25, 2011, and claims priority to U.S. Provisional Application 61/034,464, filed Mar. 6, 2008, which are hereby incorporated by reference in their entirety.

BACKGROUND OF THE INVENTION

Oncogenes are mutated forms of certain normal cellular genes ("proto-oncogenes"). In certain instances, oncogenes encode abnormal versions of signal pathway components, (e.g., receptor tyrosine kinases, serine-threonine kinases, or downstream signaling molecules.

SUMMARY OF THE INVENTION

Disclosed herein, in certain embodiments, is a crystalline polymorph Form A of N—(S)-(3,4-difluoro-2-(2-fluoro-4-iodophenylamino)-6-methoxyphenyl)-1-(2,3-dihydroxypropyl)cyclopropane-1-sulfonamide that exhibits a powder x-ray diffraction pattern substantially the same as the powder x-ray diffraction pattern shown in FIG. 1, or FIG. 2. In some embodiments, the crystalline polymorph has a melting point onset as determined by differential scanning calorimetry at about 143° C. In some embodiments, crystalline polymorph is substantially free of water, substantially free of solvent, or a combination thereof.

Disclosed herein, in certain embodiments, is a polymorphic form of N-(3,4-difluoro-2-(2-fluoro-4-iodophenylamino)-6-methoxyphenyl)-1-(2,3-dihydroxypropyl)cyclopropane-1-sulfonamide made by a method comprising the step of crystallizing amorphous N-(3,4-difluoro-2-(2-fluoro-4-iodophenylamino)-6-methoxyphenyl)-1-(2,3-dihydroxypropyl)cyclopropane-1-sulfonamide from a mixture of ethyl acetate and heptane. In some embodiments, the mixture of ethyl acetate and heptane is in a ratio of from about 1-4 parts ethyl acetate to about 2-10 parts heptane. In some embodiments, the mixture of ethyl acetate and heptane is in a ratio of from about 2 parts ethyl acetate to about 5 parts heptane.

Disclosed herein, in certain embodiments, is a pharmaceutical composition comprising a therapeutically-effective amount of a crystalline polymorph disclosed herein. In some embodiments, the composition comprises an excipient.

Disclosed herein, in certain embodiments, is a method of treating a MEK mediated disorder, comprising administering to an individual in need thereof a therapeutically-effective amount of a crystalline polymorph disclosed herein. In some embodiments, the MEK mediated disorder is a cytokine-mediated disorder. In some embodiments, the MEK mediated disorder is selected from immune disorders, inflammatory disorders, infectious disorders, proliferative disorders, or combinations thereof. In some embodiments, the MEK mediated disorder is a cancer. In some embodiments, the MEK mediated disorder is a fibrogenic disorder. In some embodiments, the method further comprises co-administering a second active agent. In some embodiments, the method further comprises co-administering a cytotoxic agent, an anti-angiogenesis agent, an anti-neoplastic agent, or combinations thereof. In some embodiments, the method further comprises surgery and/or radiation therapy.

DETAILED DESCRIPTION OF THE INVENTION

Figure 1:
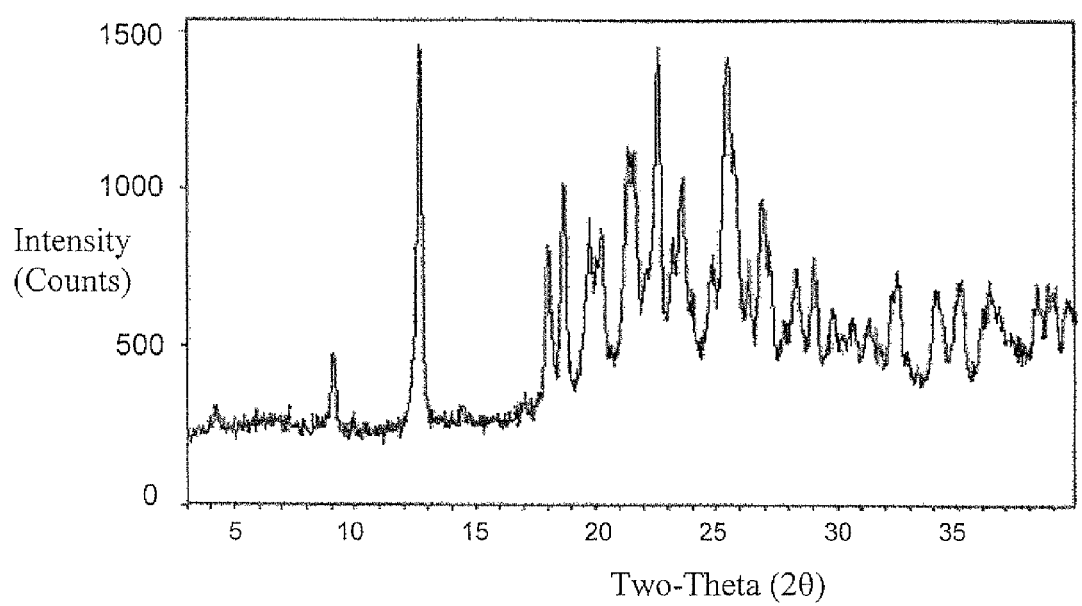
FIG. 1 is a graph of a powder x-ray diffraction (PXRD) pattern of N—(S)-(3,4-difluoro-2-(2-fluoro-4-iodophenylamino)-6-methoxyphenyl)-1-(2,3-dihydroxypropyl)cyclopropane-1-sulfonamide Form A, generated using a Inel XRG-3000 diffractometer. The graph plots the intensity of the peaks as defined by counts per second versus the diffraction angle 2θ in degrees.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

I. Certain Terminology

Unless defined otherwise, all technical and scientific terms used herein have the same meaning as is commonly understood by one of skill in the art to which the claimed subject matter belongs.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a", "an" and "the" include plural referents unless the context clearly dictates otherwise. It should also be noted that use of "or" means "and/or" unless stated otherwise. Furthermore, use of the term "including" as well as other forms, (e.g., "include", "includes", and "included" is not limiting.

Definitions of standard chemistry terms are found in reference works, including Carey and Sundberg "ADVANCED ORGANIC CHEMISTRY 4$^{TH}$ ED." Vols. A (2000) and B (2001), Plenum Press, New York. Unless specific definitions are provided, the nomenclature employed in connection with, and the laboratory procedures and techniques of, analytical chemistry, synthetic organic chemistry, and medicinal and pharmaceutical chemistry described herein are those known in the art.

The term "MEK inhibitor" as used herein refers to a compound that exhibits an $IC_{50}$ with respect to MEK activity, of no more than about 100 µM or not more than about 50 µM, as measured in the Meld kinase assay described generally herein. "$IC_{50}$" is that concentration of inhibitor which reduces the activity of an enzyme (e.g., MEK) to half-maximal level. Compounds described herein have been discovered to exhibit inhibition against MEK. Compounds of the present invention preferably exhibit an $IC_{50}$ with respect to MEK of no more than about 10 µM, more preferably, no more than about 5 µM, even more preferably not more than about 1 µM, and most preferably, not more than about 200 nM, as measured in the Meld kinase assay described herein.

The term "subject", "individual" or "individual" as used herein encompasses mammals and non-mammals. None of the terms are to be construed as requiring the supervision of a medical professional (e.g., a physician, nurse, orderly, hospice worker). Examples of mammals include, but are not limited to, any member of the Mammalian class: humans, non-human primates (e.g., chimpanzees, and other apes and monkey species); farm animals (e.g., cattle, horses, sheep, goats, swine); domestic animals (e.g., rabbits, dogs, and cats); laboratory animals including rodents, (e.g., rats, mice and guinea pigs), and the like. Examples of non-mammals include, but are not limited to, birds, fish and the like. In one embodiment of the methods and compositions provided herein, the mammal is a human.

The terms "treat," "treating" or "treatment," and other grammatical equivalents mean slowing or stopping the development of a disorder, causing regression of a disorder, ameliorating disorderthe symptoms of a disorder, preventing the development or presentation of additional symptoms, ameliorating and/or preventing the underlying cause of a symptom, or combinations thereof. Ther term further includes achieving a prophylactic benefit. For prophylactic benefit, a compound or composition disclosed herein is administered to an individual at risk of developing a particular disorder, predisposed to developing a particular disorder, or to an individualreporting one or more of the physiological symptoms of a disorder.

The terms "effective amount", "therapeutically effective amount" or "pharmaceutically effective amount" as used herein, refer to an amount of an agent or compound that is sufficient to treat a disorder. In some embodiments, the result is a reduction in and/or alleviation of the signs, symptoms, or causes of a disorder, or any other desired alteration of a biological system. For example, an "effective amount" for therapeutic uses is the amount of the composition comprising a compound as disclosed herein required to provide a clinically significant decrease in a disorder. An appropriate "effective" amount in any individual case is determined using any suitable technique, (e.g., a dose escalation study).

The terms "substantially free of water" and "substantially free of solvent" as used herein, refer to crystalline polymorph forms comprising less than 0.01, 0.1, 0.2, 0.3, 0.4, 0.5, 1 or 2% by weight of water or solvent respectively.

The term "substantially the same as" as used herein, refers to a powder x-ray diffraction pattern or differential scanning calorimetry pattern that is non-identical to those depicted herein, but that falls within the limits of experimental error, when considered by one of ordinary skill in the art.

The term "pharmaceutically acceptable" as used herein, refers to a material, (e.g., a carrier or diluent), which does not abrogate the biological activity or properties of the compounds described herein, and is relatively nontoxic (i.e., the material is administered to an individual without causing undesirable biological effects or interacting in a deleterious manner with any of the components of the composition in which it is contained).

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target.

II. MEK

In certain instances, Ras is a signal transduction protein. In certain instances, Ras is activated by the binding of guanosine nucleotides, GTP (Guanosine triphosphate) or GDP (Guanosine diphosphate).

In certain instances, the activation of Ras results in the activation of a cascade of serine/threonine kinases. In certain instances, activated Ras activates Raf proteins. In certain instances, activated Raf proteins activate "MEK1" and "MEK2."

MEK1 and MEK2 are dual-function serine/threonine and tyrosine protein kinases that, in certain instances, activate MAPK. In certain instances, activation of MAP kinase by mitogens appears induces cellular proliferation. In certain instances, constitutive activation of MAPK induces cellular transformation. In certain instances, blockade of downstream Ras signaling, as by use of a dominant negative Raf-1 protein, inhibits mitogenesis, whether induced from cell surface receptors or from oncogenic Ras mutants.

Figure 2:
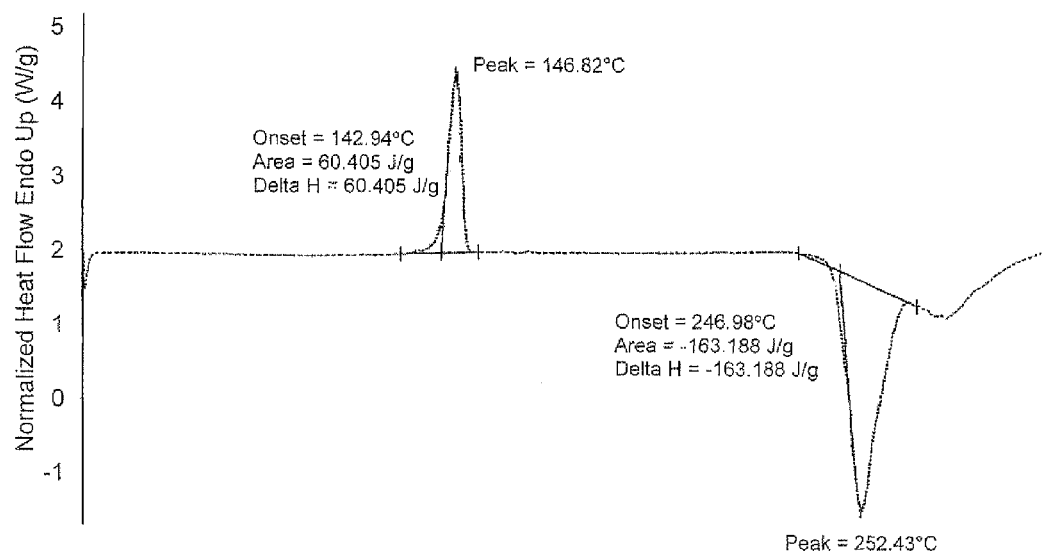
FIG. 2 is a graph of a modulated Differential Scanning calorimetry (DSC) thermogram of N—(S)-(3,4-difluoro-2-(2-fluoro-4-iodophenylamino)-6-methoxyphenyl)-1-(2,3-dihydroxypropyl)cyclopropane-1-sulfonamide Form A generated using a TA Instruments differential scanning calorimeter Q1000. The graph plots the normalized heat flow in units of Watts/gram (W/g) versus the measured sample temperature in ° C.

III. N—(S)-(3,4-difluro-2-(2-fluoro-4-iodophenylamino)-6-methoxyphenyl)-1-(2,3-dihydroxypropyl) cyclopropane-1-sulfonamide Disclosed herein, in certain embodiments, is a crystalline polymorph of N—(S)-(3,4-difluoro-2-(2-fluoro-4-iodophenylamino)-6-methoxyphenyl)-1-(2,3-dihydroxypropyl)cyclopropane-1-sulfonamide. In some embodiments, is a crystalline polymorph of a compound of structure A:

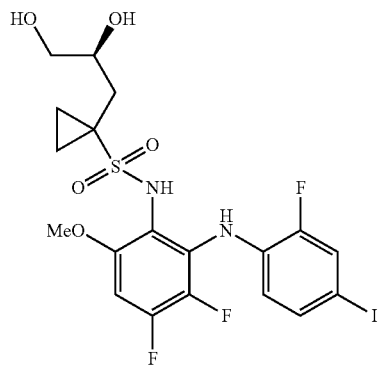

wherein the polymorph exhibits a powder x-ray diffraction pattern substantially the same as the powder x-ray diffraction pattern shown in FIG. 1, or FIG. 2. In some embodiments, the crystalline polymorph has a melting point onset as determined by differential scanning calorimetry at about 143° C.

In some embodiments, crystalline polymorph is substantially free of water, substantially free of solvent, or a combination thereof.

Disclosed herein, in certain embodiments, is a polymorphic form of N-(3,4-difluoro-2-(2-fluoro-4-iodophenylamino)-6-methoxyphenyl)-1-(2,3-dihydroxypropyl)cyclopropane-1-sulfonamide made by a method comprising the step of crystallizing amorphous N-(3,4-difluoro-2-(2-fluoro-4-iodophenylamino)-6-methoxyphenyl)-1-(2,3-dihydroxypropyl)cyclopropane-1-sulfonamide from a mixture of ethyl acetate and heptane. In some embodiments, the mixture of ethyl acetate and heptane is in a ratio of from about 1-4 parts ethyl acetate to about 2-10 parts heptane. In some embodiments, the mixture of ethyl acetate and heptane is in a ratio of from about 2 parts ethyl acetate to about 5 parts heptane.

In some embodiments, the crystaline polymorph comprises at least one of the following properties: (a) a powder x-ray diffraction pattern substantially the same as the powder x-ray diffraction pattern shown in FIG. 1, (b) a differential scanning calorimetry pattern substantially the same as the a differential scanning calorimetry pattern shown in FIG. 2, or (c) a melting point onset as determined by differential scanning calorimetry at about 143° C.

In some embodiments, the crystaline polymorph comprises at least two of the following properties: (a) a powder x-ray diffraction pattern substantially the same as the powder x-ray diffraction pattern shown in FIG. 1, (b) a differential scanning calorimetry pattern substantially the same as the a differential scanning calorimetry pattern shown in FIG. 2, or (c) a melting point onset as determined by differential scanning calorimetry at about 143° C.

In some embodiments, the crystaline polymorph comprises at least three of the following properties: (a) a powder x-ray diffraction pattern substantially the same as the powder x-ray diffraction pattern shown in FIG. 1, (b) a differential scanning calorimetry pattern substantially the same as the a differential scanning calorimetry pattern shown in FIG. 2, or (c) a melting point onset as determined by differential scanning calorimetry at about 143° C.

In some embodiments, the crystalline polymorph has a powder x-ray diffraction pattern displaying at least three of the largest peaks as the powder x-ray diffraction pattern shown in FIG. 1. In some embodiments, the crystalline polymorph has a powder x-ray diffraction pattern displaying at least four of the largest peaks as the powder x-ray diffraction pattern shown in FIG. 1. In some embodiments, the crystalline polymorph has a powder x-ray diffraction pattern displaying at least five of the largest peaks as the powder x-ray diffraction pattern shown in FIG. 1. In some embodiments, the crystalline polymorph has a powder x-ray diffraction pattern displaying at least six of the largest peaks as the powder x-ray diffraction pattern shown in FIG. 1.

IV. Methods of Use

In some embodiments, a compound or composition disclosed herein is administered to inhibit a MEK enzyme in an individual in need thereof. In some embodiments, a compound or composition disclosed herein is administered to treat a disorder in an individual in need thereof. In some embodiments, a compound or composition disclosed herein is administered to treat a MEK-mediated disorder in an individual in need thereof. In some embodiments, a compound or composition disclosed herein is administered to treat a proliferative disorder in an individual in need thereof. In some embodiments, a compound or composition disclosed herein is administered to treat an inflammatory disorder in an individual in need thereof.

In some embodiments, a compound or composition disclosed herein is administered to inhibit a MEK enzyme in an individual in need thereof. In some embodiments, the MEK enzyme is MEK kinase. In some embodiments, MEK enzyme is MEK1. In some embodiments, the MEK enzyme is MEK2.

In some embodiments, a MEK enzyme is at least about 1% inhibited. In some embodiments, a MEK enzyme is at least about 2% inhibited. In some embodiments, a MEK enzyme is at least about 3% inhibited. In some embodiments, a MEK enzyme is at least about 4% inhibited. In some embodiments, a MEK enzyme is at least about 5% inhibited. In some embodiments, a MEK enzyme is at least about 10% inhibited. In some embodiments, a MEK enzyme is at least about 20% inhibited. In some embodiments, a MEK enzyme is at least about 25% inhibited. In some embodiments, a MEK enzyme is at least about 30% inhibited. In some embodiments, a MEK enzyme is at least about 40% inhibited. In some embodiments, a MEK enzyme is at least about 50% inhibited. In some embodiments, a MEK enzyme is at least about 60% inhibited. In some embodiments, a MEK enzyme is at least about 70% inhibited. In some embodiments, a MEK enzyme is at least about 75% inhibited. In some embodiments, a MEK enzyme is at least about 80% inhibited. In some embodiments, a MEK enzyme is at least about 90% inhibited. In some embodiments, a MEK enzyme is essentially completely inhibited.

In some embodiments, a compound and/or composition disclosed herein is administered to treat a MEK mediated disorder in an individual in need thereof. In some embodiments, the MEK mediated disorder is an inflammatory disorder, a proliferative disorder, an infection, an immune disorder (e.g., autoimmune disorders, psoriasis, rheumatoid arthritis, osteoarthritis, dry eye, and/or glaucomas), a cardiac disorder (e.g., stroke, reperfusion injury, ischemia, atherosclerosis, heart failure), a neurological disorder, a fibrogenetic disorder, a metabolic disease, chronic pain, and/or neuropathic pain.

In some embodiments, a compound and/or composition disclosed herein is administered to treat an immune disorder. In some embodiments, a compound and/or composition disclosed herein is administered to treat a cytokine-mediate disorder (i.e., disorders resulting from the excessive or unregulated production of pro-inflammatory cytokines including for example TNF, IL-1, IL-6 and IL-8). In some embodiments, a compound and/or composition disclosed herein is administered to treat an autoimmune disorder, an inflammatory disorder, an infectious disorder, a prostaglandin endoperoxidase synthetase-2 (COX-2)-mediated disorder, rheumatoid arthritis, inflammatory bowel disorder, inflammatory pain, ulcerative colitis, Crohn's disorder, periodontal disorder, temporomandibular joint disorder, multiple sclerosis, diabetes, glomerulonephritis, systemic lupus erythematosus, scleroderma, chronic thyroiditis, Grave's disorder, hemolytic anemia, autoimmune gastritis, autoimmune neutropenia, thrombocytopenia, chronic active hepatitis, myasthenia gravis, atopic dermatitis, graft vs. host disorder, psoriasis, asthma, allergies, respiratory distress syndrome, acute or chronic pancreatitis, and/or multiple sclerosis.

In some embodiments, a compound and/or composition disclosed herein is administered to treat an inflammatory disorder. In some embodiments, the inflammatory disorder is proliferative glomerulonephritis, chronic inflammatory disorder, bursitis, acute rheumatic arthritis, allergies, bursitis, pulmonary fibrosis, pyogenic arthritis, ankylosing spondylitis, arthritis, asthma, atherosclerosis, chronic inflammatory disorder, chronic obstructive pulmonary disease, diabetes (including diabetic retinopathy), diarrhea, eczema, enteropathic arthritis, gastritis, gout, gouty arthritis, inflammatory bowel disorder, irritable bowel syndrome, ulcerative colitis, juvenile arthritis, neuropathic arthritis, organ transplant rejection, osteoarthritis, osteoporosis, pancreatitis, proliferative glomerulonephritis, pruritis, psoriasis, psoriatic arthritis, pulmonary fibrosis, pulmonary inflammation, pyogenic arthritis, reflux esophagitis, respiratory distress syndrome, acute or chronic pancreatitis, rheumatoid arthritis, scleroderma, cystic fibrosis, systemic lupus erythematosus, tendonitis, ulcerative colitis, vitaligo, spondyloarthropathies, or Crohn's disorder.

In some embodiments, a compound and/or composition disclosed herein is administered to treat a proliferative disorder in an individual in need thereof. In some embodiments, the proliferative disorder is an abnormal cell growth. In some embodiments, the proliferative disorder is a hemangioma. In some embodiments, the proliferative disorder is a cancer. In some embodiments, the cancer is a hematologic cancer and/or nonhematologic cancer. In some embodiments, the cancer is multiple myeloma, a leukemia, and/or a lymphoma. In some embodiments, the cancer is an acute leukemia, and/or a chronic leukemia. In some embodiments, the cancer is acute lymphocytic leukemia (ALL) and/or acute nonlymphocytic leukemia (ANLL). In some embodiments, the cancer is chronic lymphocytic leukemia (CLL) and/or chronic myelogenous leukemia (CML). In some embodiments, the cancer is Hodgkin's lymphoma and/or non-Hodgkin's lymphoma. In some embodiments, the cancer is multiple myeloma. In some embodiments, the cancer is of low, intermediate, or high grade. In some embodiments, the cancer is: brain cancer, a cancer of the head and/or neck, lung cancer, breast cancer, a cancer of the reproductive system, a cancer of the digestive system, pancreatic cancer, and/or a cancer of the urinary system. In some embodiments, the cancer is a cancer of the upper digestive tract or colorectal cancer. In some embodiments, the cancer is bladder cancer or renal cell carcinoma. In some embodiments, the cancer is prostate cancer. In some embodiments, the cancer is breast cancer (e.g., a ductal carcinoma in duct tissue in a mammary gland, medullary carcinomas, colloid carcinomas, tubular carcinomas, and/or inflammatory breast cancer; ovarian cancer, including epithelial ovarian tumors (e.g., adenocarcinoma in the ovary and/or an adenocarcinoma that has migrated from the ovary into the abdominal cavity; uterine cancer; cervical cancer (e.g., (e.g., adenocarcinoma in the cervix epithelial including squamous cell carcinoma and/or adenocarcinoma); prostate cancer (e.g., (e.g., prostate cancer selected from the following: an adenocarcinoma or an adenocarinoma that has migrated to the bone); pancreatic cancer (e.g., epitheliod carcinoma in the pancreatic duct tissue and/or an adenocarcinoma in a pancreatic duct); bladder cancer (e.g., (e.g., a transitional cell carcinoma in urinary bladder, urothelial carcinomas (transitional cell carcinomas), tumors in the urothelial cells that line the bladder, squamous cell carcinomas, adenocarcinomas, and/or small cell cancers); leukemia (e.g., acute myeloid leukemia (AML), acute lymphocytic leukemia, chronic lymphocytic leukemia, chronic myeloid leukemia, hairy cell leukemia, myelodysplasia, and/or a myeloproliferative disorder); bone cancer; lung cancer (e.g., non-small cell lung cancer (NSCLC), which is divided into squamous cell carcinomas, adenocarcinomas, and/or large cell undifferentiated carcinomas, and/or small cell lung cancer); skin cancer (e.g., basal cell carcinoma, melanoma, squamous cell carcinoma and/or actinic keratosis); eye retinoblastoma; cutaneous or intraocular (eye) melanoma; primary liver cancer (cancer that begins in the liver); kidney cancer; thyroid cancer (e.g., papillary, follicular, medullary and/or anaplastic); AIDS-related lymphoma (e.g., diffuse large B-cell lymphoma, B-cell immunoblastic lymphoma and/or small non-cleaved cell lymphoma); Kaposi's Sarcoma; viral-induced cancers (e.g., hepatitis B virus (HBV), hepatitis C virus (HCV), and/or hepatocellular carcinoma); human lymphotropic virus-type 1 (HTLV-1) and/or adult T-cell leukemia/lymphoma; human papilloma virus (HPV) cervical cancer; a central nervous system cancer (CNS) (e.g., primary brain tumor, which includes gliomas (astrocytoma, anaplastic astrocytoma, or glioblastoma multiforme), Oligodendroglioma, Ependymoma, Meningioma, Lymphoma, Schwannoma, and/or Medulloblastoma); a peripheral nervous system (PNS) cancer (e.g., acoustic neuromas and/or malignant peripheral nerve sheath tumor (MP-NST) including neurofibromas and/or schwannomas, malignant fibrous cytoma, malignant fibrous histiocytoma, malignant meningioma, malignant mesothelioma, and/or malignant mixed Müllerian tumor); an oral cavity or oropharyngeal cancer (e.g., hypopharyngeal cancer, laryngeal cancer, nasopharyngeal cancer, and/or oropharyngeal cancer); stomach cancer (e.g., lymphomas, gastric stromal tumors, and/or carcinoid tumors); testicular cancer (e.g., germ cell tumors (GCTs), which include seminomas and/or nonseminomas, and/or gonadal stromal tumors, which include Leydig cell tumors and/or Sertoli cell tumors); thymus cancer (e.g., thymomas, thymic carcinomas, Hodgkin disorder, non-Hodgkin lymphomas carcinoids or carcinoid tumors); rectal cancer; colon cancer, renal cancer, adrenocortical carcinoma, follicular lymphoma, pre-B acute leukemia, chronic lymphocytic B-leukemia, adenocarcinoma, angiosarcoma, astrocytoma, acoustic neuroma, anaplastic astrocytoma, basal cell carcinoma, blastoglioma, chondrosarcoma, choriocarcinoma, chordoma, craniopharyngioma, cutaneous melanoma, cystadenocarcinoma, endotheliosarcoma, embryonal carcinoma, ependymoma, Ewing's tumor, epithelial carcinoma, fibrosarcoma, gastric cancer, genitourinary tract cancers, glioblastoma multiforme, hemangioblastoma, hepatocellular carcinoma, hepatoma, Kaposi's sarcoma, large cell carcinoma, leiomyosarcoma, liposarcoma, lymphangiosarcoma, lymphangioendotheliosarcoma, medullary thyroid carcinoma, medulloblastoma, meningioma mesothelioma, myelomas, myxosarcoma neuroblastoma, neurofibrosarcoma, oligodendroglioma, osteogenic sarcoma, epithelial ovarian cancer, papillary carcinoma, papillary adenocarcinomas, parathyroid tumors, pheochromocytoma, pinealoma, plasmacytomas, retinoblastoma, rhabdomyosarcoma, sebaceous gland carcinoma, seminoma, skin cancers, melanoma, small cell lung carcinoma, squamous cell carcinoma, sweat gland carcinoma, synovioma, thyroid cancer, uveal melanoma, Wiles tumor, a cancer of oral cavity and/or pharynx, a cancer of the respiratory system, a cancers of a bone and/or joint, a cancer of soft tissue, a skin cancer, a cancer of the genital system, a cancers of the eye and/or orbit, a cancers of the nervous system, a cancer of the lymphatic system, and/or a cancer of the endocrine system. In certain embodiments, these cancer is cancer of the tongue, mouth, pharynx, or other oral cavity; esophageal cancer, stomach cancer, or cancer of the small intestine; colon cancer or rectal, anal, or anorectal cancer; cancer of the liver, intrahepatic bile duct, gallbladder, pancreas, or other biliary or digestive organs; laryngeal, bronchial, or other cancers of the respiratory organs; heart cancer, melanoma, basal cell carcinoma, squamous cell carcinoma, other non-epithelial skin cancer; uterine or cervical cancer; uterine corpus cancer; ovarian, vulvar, vaginal, or other female genital cancer; prostate, testicular, penile or other male genital cancer; urinary bladder cancer; cancer of the kidney; renal, pelvic, or urethral cancer or other cancer of the genito-urinary organs; thyroid cancer or other endocrine cancer; chronic lymphocytic leukemia; and/orcutaneous T-cell lymphoma, both granulocytic monocytic.

In some embodiments, a compound and/or composition disclosed herein is administered to treat a proliferative disorder in an individual in need thereof. In some embodiments, the proliferative disorder is a fibrogenic disorder. In some embodiments, the proliferative disorder an angiogenesis-related condition or disorder, angioplasty, atherosclerosis, cardiac hypertrophy, hyperplasias, an immune disorder, inflammation, interstitial nephritis or pulmonary fibrosis, keloid formation, liver cirrhosis, migraine, pain, polymyositis, proliferation induced after a medical procedure, restenosis, rheumatoid arthritis, scleroderma, systemic lupus, and/or vasculogenesis.

In some embodiments, a compound and/or composition disclosed herein is administered to treat a proliferative disorder in an individual in need thereof. In some embodiments, the proliferative disorder is benign hyperplasia of the skin (e.g., psoriasis), or prostate (e.g., benign prostatic hypertrophy (BPH)).

In some embodiments, a compound and/or composition disclosed herein is administered to treat a hematologic disorder in an individual in need thereof. In some embodiments, the hematologic disorder is sickle cell anemia, myelodysplastic disorders (MDS), and/or myeloproliferative disorders. In further embodiments, the proliferative disorder is polycythemia vera, myelofibrosis and/or essential thrombocythemia.

In some embodiments, a compound and/or composition disclosed herein is administered to treat a ophthalmologic disorder in an individual in need thereof. In some embodiments, the ophthalmologic disorder is dry eye (including Sjogren's syndrome), macular degeneration, closed and/or wide angle glaucoma, retinal ganglion degeneration, occular ischemia, retinitis, retinopathies (e.g., glaucomatous retinopathy or diabetic retinopathy), uveitis, ocular photobia, of inflammation and/or pain associated with trauma to the eye tissue (e.g., post-Operative inflammation or pain from ophthalmic surgery (e.g., cataract surgery and/or refractive surgery)).

In some embodiments, a compound and/or composition disclosed herein is administered to treat a dermatologic disorder in an individual in need thereof. In some embodiments, the dermatologic disorder is melanoma, basel cell carcinoma, squamous cell carcinoma, psoriasis and/or persistent itch.

In some embodiments, a compound and/or composition disclosed herein is administered to treat a metabolic disorder in an individual in need thereof. In some embodiments, the metabolic disorder is metabolic syndrome, insulin resistance, Type 1 diabetes, and/or Type 2 diabetes.

In some embodiments, a compound and/or composition disclosed herein is administered to treat a disorder associated with tissue damage in an individual in need thereof. In some embodiments, the disorder associated with tissue damage is a vascular disorder, a migraine headache, periarteritis nodosa, thyroiditis, aplastic anemia, Hodgkin's disorder, sclerodoma, rheumatic fever, type I diabetes, neuromuscular junction disorder including myasthenia gravis, white matter disorder including multiple sclerosis, sarcoidosis, nephritis, nephrotic syndrome, Behcet's syndrome, polymyositis, periodontis, hypersensitivity, swelling occurring after injury, ischemias including myocardial ischemia, cardiovascular ischemia, ischemia secondary to cardiac arrest, allergic rhinitis, respiratory distress syndrome, endotoxin shock syndrome, and/or atherosclerosis.

In some embodiments, a compound and/or composition disclosed herein is administered to treat a cardiovascular disorder in an individual in need thereof. In some embodiments, the cardiovascular disorder is atherosclerosis, cardiac hypertrophy, idiopathic cardiomyopathies, heart failure, angiogenesis-related conditions or disorders, and/or proliferation induced after a medical procedure, including, but not limited to restenosis resulting from surgery and/or angioplasty.

In some embodiments, a compound and/or composition disclosed herein is administered to treat a neurological disorder associated with tissue damage in an individual in need thereof. In some embodiments, the neurological disorder is Parkinson's disorder; Alzheimer's disorder; Alzheimer's dementia; central nervous system damage resulting from stroke, ischemia and/or trauma; epilepsy; neuropathic pain, depression; and/or bipolar disorders.

In some embodiments, a compound and/or composition disclosed herein is administered to prevent blastocyte implantation.

In some embodiments, a compound and/or composition disclosed herein is administered to degrade, inhibit the growth of or to kill a cell. In some embodiments, the cell is a cancer cell. In some embodiments, the cell is a brain, breast, lung, ovarian, pancreatic, prostate, renal, or colorectal cancer cell.

In some embodiments, a compound and/or composition disclosed herein is administered to inhibit the growth of a target cell. In some embodiments, the growth of a target cell is about 1% inhibited relative to the growth rate preceeding administration of a compound and/or composition disclosed herein. In some embodiments, the growth of a target cell is about 2% inhibited inhibited relative to the growth rate preceeding administration of a compound and/or composition disclosed herein. In some embodiments, the growth of a target cell is about 3% inhibited inhibited relative to the growth rate preceeding administration of a compound and/or composition disclosed herein. In some embodiments, the growth of a target cell is about 4% inhibited inhibited relative to the growth rate preceeding administration of a compound and/or composition disclosed herein. In some embodiments, the growth of a target cell is about 5% inhibited inhibited relative to the growth rate preceeding administration of a compound and/or composition disclosed herein. In some embodiments, the growth of a target cell is about 10% inhibited inhibited relative to the growth rate preceeding administration of a compound and/or composition disclosed herein. In some embodiments, the growth of a target cell is about 20% inhibited inhibited relative to the growth rate preceeding administration of a compound and/or composition disclosed herein. In some embodiments, the growth of a target cell is about 25% inhibited inhibited relative to the growth rate preceeding administration of a compound and/or composition disclosed herein. In some embodiments, the growth of a target cell is about 30% inhibited inhibited relative to the growth rate preceeding administration of a compound and/or composition disclosed herein. In some embodiments, the growth of a target cell is about 40% inhibited inhibited relative to the growth rate preceeding administration of a compound and/or composition disclosed herein. In some embodiments, the growth of a target cell is about 50% inhibited inhibited relative to the growth rate preceeding administration of a compound and/or composition disclosed herein. In some embodiments, the growth of a target cell is about 60% inhibited inhibited relative to the growth rate preceeding administration of a compound and/or composition disclosed herein. In some embodiments, the growth of a target cell is about 70% inhibited inhibited relative to the growth rate preceeding administration of a compound and/or composition disclosed herein. In some embodiments, the growth of a target cell is about 75% inhibited inhibited relative to the growth rate preceeding administration of a compound and/or composition disclosed herein. In some embodiments, the growth of a target cell is about 80% inhibited inhibited relative to the growth rate preceeding administration of a compound and/or composition disclosed herein. In some embodiments, the growth of a target cell is about 90% inhibited inhibited relative to the growth rate preceeding administration of a compound and/or composition disclosed herein. In some embodiments, the growth of a target cell is about 100% inhibited inhibited relative to the growth rate preceeding administration of a compound and/or composition disclosed herein. In some embodiments, the target cell is a cancer cell.

In some embodiments, a compound and/or composition disclosed herein is administered to degrade a target cell. In some embodiments, a compound and/or composition disclosed herein is administered to degrade a plurality of target cells. In some embodiments, 1% of the target cells are degraded. In some embodiments, 2% of the target cells are degraded. In some embodiments, 3% of the target cells are degraded. In some embodiments, 4% of the target cells are degraded. In some embodiments, 5% of the target cells are degraded. In some embodiments, 10% of the target cells are degraded. In some embodiments, 20% of the target cells are degraded. In some embodiments, 25% of the target cells are degraded. In some embodiments, 30% of the target cells are degraded. In some embodiments, 40% of the target cells are degraded. In some embodiments, 50% of the target cells are degraded. In some embodiments, 60% of the target cells are degraded. In some embodiments, 70% of the target cells are degraded. In some embodiments, 75% of the target cells are degraded. In some embodiments, 80% of the target cells are degraded. In some embodiments, 90% of the target cells are degraded. In some embodiments, 100% of the target cells are degraded. In some embodiments, essentially all of the target cells are degraded. In some embodiments, the target cells are cancer cells.

In some embodiments, a compound and/or composition disclosed herein is administered to kill a target cell. In some embodiments, a compound and/or composition disclosed herein is administered to kill a plurality of target cells. In some embodiments, 1% of the target cells are killed. In some embodiments, 2% of the target cells are killed. In some embodiments, 3% of the target cells are killed. In some embodiments, 4% of the target cells are killed. In some embodiments, 5% of the target cells are killed. In some embodiments, 10% of the target cells are killed. In some embodiments, 20% of the target cells are killed. In some embodiments, 25% of the target cells are killed. In some embodiments, 30% of the target cells are killed. In some embodiments, 40% of the target cells are killed. In some embodiments, 50% of the target cells are killed. In some embodiments, 60% of the target cells are killed, In some embodiments, 70% of the target cells are killed. In some embodiments, 75% of the target cells are killed. In some embodiments, 80% of the target cells are killed. In some embodiments, 90% of the target cells are killed. In some embodiments, 100% of the target cells are killed. In some embodiments, the target cells are cancer cells.

In some embodiments, a compound and/or composition disclosed herein is administered to reduce the size of a tumor, inhibit tumor growth, reduce metastasis or prevent metastasis in an individual in need thereof.

In some embodiments, the size of a tumor is reduced. In some embodiments, the size of a tumor is reduced by at least 1%. In some embodiments, the size of a tumor is reduced by at least 2%. In some embodiments, the size of a tumor is reduced by at least 3%. In some embodiments, the size of a tumor is reduced by at least 4%. In some embodiments, the size of a tumor is reduced by at least 5%. In some embodiments, the size of a tumor is reduced by at least 10%. In some embodiments, the size of a tumor is reduced by at least 20%. In some embodiments, the size of a tumor is reduced by at least 25%. In some embodiments, the size of a tumor is reduced by at least 30%. In some embodiments, the size of a tumor is reduced by at least 40%. In some embodiments, the size of a tumor is reduced by at least 50%. In some embodiments, the size of a tumor is reduced by at least 60%. In some embodiments, the size of a tumor is reduced by at least 70%. In some embodiments, the size of a tumor is reduced by at least 75%. In some embodiments, the size of a tumor is reduced by at least 80%. In some embodiments, the size of a tumor is reduced by at least 85%. In some embodiments, the size of a tumor is reduced by at least 90%. In some embodiments, the size of a tumor is reduced by at least 95%.

In some embodiments, tumor growth is inhibited. In some embodiments, tumor growth is inhibited by at least 1% relative to the growth rate preceeding administration of a compound and/or composition disclosed herein. In some embodiments, tumor growth is inhibited by at least 2% relative to the growth rate preceeding administration of a compound and/or composition disclosed herein. In some embodiments, tumor growth is inhibited by at least 3% relative to the growth rate preceeding administration of a compound and/or composition disclosed herein. In some embodiments, tumor growth is inhibited by at least 4% relative to the growth rate preceeding administration of a compound and/or composition disclosed herein. In some embodiments, tumor growth is inhibited by at least 5% relative to the growth rate preceeding administration of a compound and/or composition disclosed herein. In some embodiments, tumor growth is inhibited by at least 6% relative to the growth rate preceeding administration of a compound and/or composition disclosed herein. In some embodiments, tumor growth is inhibited by at least 10% relative to the growth rate preceeding administration of a compound and/or composition disclosed herein. In some embodiments, tumor growth is inhibited by at least 20% relative to the growth rate preceeding administration of a compound and/or composition disclosed herein. In some embodiments, tumor growth is inhibited by at least 30% relative to the growth rate preceeding administration of a compound and/or composition disclosed herein. In some embodiments, tumor growth is inhibited by at least 40% relative to the growth rate preceeding administration of a compound and/or composition disclosed herein. In some embodiments, tumor growth is inhibited by at least 50% relative to the growth rate preceeding administration of a compound and/or composition disclosed herein. In some embodiments, tumor growth is inhibited by at least 60% relative to the growth rate preceeding administration of a compound and/or composition disclosed herein. In some embodiments, tumor growth is inhibited by at least 70% relative to the growth rate preceeding administration of a compound and/or composition disclosed herein. In some embodiments, tumor growth is inhibited by at least 75% relative to the growth rate proceeding administration of a compound and/or composition disclosed herein. In some embodiments, tumor growth is inhibited by at least 80% relative to the growth rate preceeding administration of a compound and/or composition disclosed herein. In some embodiments, tumor growth is inhibited by at least 90% relative to the growth rate preceeding administration of a compound and/or composition disclosed herein. In some embodiments, tumor growth is inhibited by at least 95% relative to the growth rate preceeding administration of a compound and/or composition disclosed herein. In some embodiments, tumor growth is inhibited by at least 99% relative to the growth rate preceeding administration of a compound and/or composition disclosed herein.

In some embodiments, metastasis is inhibited. In some embodiments, metastasis is inhibited by at least 1% relative to the growth rate preceeding administration of a compound and/or composition disclosed herein. In some embodiments, metastasis is inhibited by at least 2% relative to the growth rate proceeding administration of a compound and/or composition disclosed herein. In some embodiments, metastasis is inhibited by at least 3% relative to the growth rate preceeding administration of a compound and/or composition disclosed herein. In some embodiments, metastasis is inhibited by at least 4% relative to the growth rate preceeding administration of a compound and/or composition disclosed herein. In some embodiments, metastasis is inhibited by at least 5% relative to the growth rate preceeding administration of a compound and/or composition disclosed herein. In some embodiments, metastasis is inhibited by at least 6% relative to the growth rate preceeding administration of a compound and/or composition disclosed herein. In some embodiments, metastasis is inhibited by at least 10% relative to the growth rate preceeding administration of a compound and/or composition disclosed herein. In some embodiments, metastasis is inhibited by at least 20% relative to the growth rate proceeding administration of a compound and/or composition disclosed herein. In some embodiments, metastasis is inhibited by at least 30% relative to the growth rate preceeding administration of a compound and/or composition disclosed herein. In some embodiments, metastasis is inhibited by at least 40% relative to the growth rate preceeding administration of a compound and/or composition disclosed herein. In some embodiments, metastasis is inhibited by at least 50% relative to the growth rate preceeding administration of a compound and/or composition disclosed herein. In some embodiments, metastasis is inhibited by at least 60% relative to the growth rate proceeding administration of a compound and/or composition disclosed herein. In some embodiments, metastasis is inhibited by at least 70% relative to the growth rate preceeding administration of a compound and/or composition disclosed herein. In some embodiments, metastasis is inhibited by at least 75% relative to the growth rate preceeding administration of a compound and/or composition disclosed herein. In some embodiments, metastasis is inhibited by at least 80% relative to the growth rate preceeding administration of a compound and/or composition disclosed herein. In some embodiments, metastasis is inhibited by at least 90% relative to the growth rate preceeding administration of a compound and/or composition disclosed herein. In some embodiments, metastasis is inhibited by at least 95% relative to the growth rate preceeding administration of a compound and/or composition disclosed herein. In some embodiments, metastasis is inhibited by at least 99% relative to the growth rate preceeding administration of a compound and/or composition disclosed herein. In some embodiments, metastasis is prevented.

In some embodiments, a compound or composition disclosed herein is utilized for diagnostic purposes and/or as a research reagent. In some embodiments, a compound and/or composition disclosed herein is used in a differential and/or combinatorial analysis to elucidate expression patterns of genes expressed within cells and/or tissues.

IV. Pharmaceutical Compositions

Disclosed herein, in certain embodiments, is a pharmaceutical composition comprising a crystalline polymorph of N—(S)-(3,4-difluoro-2-(2-fluoro-4-iodophenylamino)-6-methoxyphenyl)-1-(2,3-dihydroxypropyl)cyclopropane-1-sulfonamide.

In some embodiments, the composition comprises a crystalline polymorph of N—(S)-(3,4-difluoro-2-(2-fluoro-4-iodophenylamino)-6-methoxyphenyl)-1-(2,3-dihydroxypropyl)cyclopropane-1-sulfonamide. In some embodiments, is a crystalline polymorph of a compound of structure A:

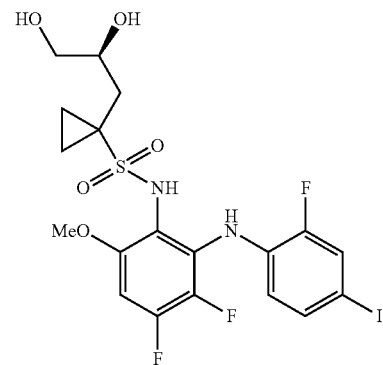

wherein the polymorph exhibits a powder x-ray diffraction pattern substantially the same as the powder x-ray diffraction pattern shown in FIG. 1.

In some embodiments, the composition comprises a crystalline polymorph of N—(S)-(3,4-difluoro-2-(2-fluoro-4-iodophenyl amino)-6-methoxyphenyl)-1-(2,3-dihydroxypropyl)cyclopropane-1-sulfonamide. In some embodiments, is a crystalline polymorph of a compound of structure A:

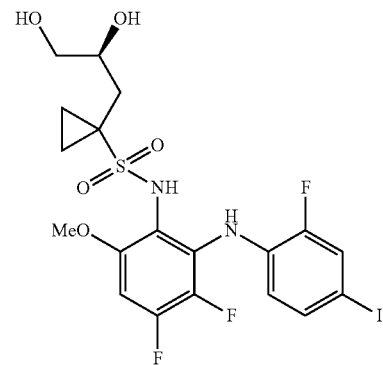

wherein the polymorph exhibits a differential scanning calorimetry pattern substantially the same as the differential scanning calorimetry pattern shown in FIG. 2.

In some embodiments, the pharmaceutical composition comprises: the polymorphic form of N-(3,4-difluoro-2-(2-fluoro-4-iodophenylamino)-6-methoxyphenyl)-1-(2,3-dihydroxypropyl) cyclopropane-1-sulfonamide made by a method comprising the step of crystallizing amorphous N-(3,4-difluoro-2-(2-fluoro-4-iodophenylamino)-6-methoxyphenyl)-1-(2,3-dihydroxypropyl)cyclopropane-1-sulfonamide. In some embodiments, the crystallization step comprises crystallizing from a mixture of ethyl acetate and heptane, for example, a mixture of ethyl acetate and heptane is in a ratio of from about 1-4 parts ethyl acetate to about 2-10 parts heptane or more specifically, a ratio of from about 2 parts ethyl acetate to about 5 parts heptane.

In some embodiments, the pharmaceutical composition further comprises at least one pharmaceutically acceptable carrier. In some embodiments, the pharmaceutical composition further comprises an adjuvant, excipient, preservative, agent for delaying absorption, filler, binder, adsorbent, buffer, disintegrating agent, and/or solubilizing agent.

In some embodiments, the pharmaceutical composition further comprises at least one pharmaceutically acceptable carrier. Suitable pharmaceutical carriers include inert diluents or fillers, water and/or various organic solvents.

In some embodiments, the composition includes a filler or diluent. In various embodiments, the filler or diluent is microcrystalline cellulose, silicified microcrystalline cellulose, lactose, mannitol, compressible sugar, calcium phosphate, calcium sulfate, calcium carbonate, calcium silicate and/or starch. In other embodiments, the filler or diluent is microcrystalline cellulose.

In some embodiments, the composition includes a disintegrant. In various embodiments, the disintegrant is croscarmellose sodium, sodium starch glycolate, crospovidone, methylcellulose, alginic acid, sodium alginate, starch derivatives, betonite and/or veegum. In some embodiment, the disintegrant is croscarmellose sodium.

In some embodiments, the composition includes a lubricant. In various embodiments, the lubricant is magnesium stearate, metallic stearates, talc, sodium stearyl fumarate and/or stearic acid. In some embodiments, the lubricant is magnesium stearate.

In some embodiments, the composition includes a wetting agent or surfactant. In various embodiments, the wetting agent or surfactant is sodium lauryl sulfate, glycerol, sorbitan oleates, sorbitan stearates, polyoxyethylenated sorbitan laurate, palmitate, stearate, oleate or hexaolate, polyoxyethylene stearyl alcohol and/or sorbitan monolaurate. In some embodiments, the wetting agent or surfactant is sodium lauryl sulfate.

Additional excipients (e.g., glidants, flavors, and/or colorants) can also be added. For additional excipients see The Handbook of Pharmaceutical Excipients, $5^{th}$ Edition, 2005 and/or the FDA Inactive Ingredient database.

In some embodiments, the composition comprises microcrystalline cellulose. In some embodiments, the composition comprises croscarmellose sodium. In some embodiments, the composition comprises sodium lauryl sulfate. In some embodiments, the composition comprises magnesium stearate.

In some embodiments, the composition further comprises a filler selected from microcrystalline cellulose, silicified microcrystalline cellulose, lactose, a compressible sugar, xylitol, sorbitol, mannitol, pregelatinized starch, maltodextrin, calcium phosphate, calcium carbonate, starch and/or a calcium silicate. In some embodiments, the composition further comprises a disintegrant selected from croscarmellose sodium, sodium starch glycolate, crospovidone, methylcellulose, alginic acid, sodium alginate, starch derivatives, betonite and/or veegum. In some embodiments, the composition further comprises a lubricant selected from magnesium stearate, metallic stearates, talc, sodium stearyl fumarate and/or stearic acid. In some embodiments, the composition further comprises a wetting agent or surfactant selected from sodium lauryl sulfate, glycerol, sorbitan oleates, sorbitan stearates, polyoxyethylenated sorbitan laurate, palmitate, stearate, oleate or hexaolate, polyoxyethylene stearyl alcohol and/or sorbitan monolaurate.

Dosage Forms

In some embodiments, a composition disclosed herein is formulated for oral administration. In some embodiments, a composition disclosed herein is administered as a tablet, capsule, pill, powder, solution, suspension, a gel cap, a caplet, a pellet, or a bead.

In some embodiments, a compositing disclosed herein is administered via a tablet. In some embodiments, a tablet comprises an inert diluent (e.g., calcium carbonate, sodium carbonate, lactose, calcium phosphate or sodium phosphate); a granulating and/or disintegrating agent (e.g., croscarmellose sodium, crospovidone or sodium starch glycolate); a filler (e.g., microcrystalline cellulose, silicified microcrystalline cellulose, pregelatinized starch, lactose, dicalcium phosphate, or compressible sugar); a binder (e.g., hypromellose, povidone, starch, gelatin, polyvinyl-pyrrolidone, or acacia); a surfactant (e.g., sodium lauryl sulfate) and/or a lubricant and/or processing aide (e.g., talc, sodium croscarmellose, corn starch, or alginic acid, magnesium stearate, stearic acid, colloidal silicon dioxide, and/or sodium lauryl sulfate). In some embodiments, a tablet further comprises a sweetening agent, a flavoring agent, a coloring agent and/or a preserving agent.

In some embodiments, a tablet comprises citric acid, a disintegrant (e.g., starch, alginic acid and/or certain complex silicates), and/or a binding agent (e.g., sucrose, gelatin and/or acacia).

In some embodiments, the tablet is un-coated or coated. In certain instances, a coating masks the taste of a composition. In certain instances, a coating modifies disintegration and/or absorption in the gastrointestinal tract.

In some embodiments, a tablet disclosed herein is prepared according to any suitable method. In some embodiments, a tablet disclosed herein is prepared by dry blending. In some embodiments, a compound disclosed herein is incorporated into the dosage form by dry blending with an excipient followed by compression into a tablet form. In some embodiments, a compressed tablet is prepared by compressing in a suitable machine the active ingredient in a free-flowing form (e.g., a powder or granules), optionally mixed with a binder, an inert diluent, and/or a lubricating, surface active or dispersing agent.

In some embodiments, a tablet disclosed herein is prepared according to any suitable method. In some embodiments, a tablet disclosed herein is prepared by wet granulation. In some embodiments, a compound disclosed herein is added to the dry excipients and mixed prior to the addition of the binder solution, or the drug substance is dissolved and added as a solution as part of granulation. In the wet granulation technique the surfactant, if used, is added to the dry excipients or added to the binder solution and incorporated in a solution form.

In some embodiments, a compositing disclosed herein is administered via a capsule. In some embodiments, the capsule is a hard capsule. In some embodiments, the active ingredient is mixed with an inert solid diluent, for example, calcium carbonate, calcium phosphate or kaolin. In some embodiments, the capsule is a soft capsule. In some embodiments, the active ingredient is mixed with water soluble carrier such as polyethyleneglycol or an oil medium, for example peanut oil, liquid paraffin, or olive oil.

In some embodiments, a capsule disclosed herein is prepared according to any suitable method. In some embodiments, a compound disclosed herein is dissolved in a material (e.g., a molten form of a high molecular weight polyethylene glycol) that is filled into a hard gelatin capsule shell that is subsequently banded and sealed. In some embodiments, a compound disclosed herein is dissolved a molten form of a high molecular weight polyethylene glycol. In some embodiments, the mixture is cooled and then filled into a gelatin capsule.

In some embodiments, the composition is in the form of a capsule or tablet and/or has a total weight of about 50 mg to about 1000 mg. In some embodiments, the composition is in the form of a capsule or tablet and/or has a total weight selected from the group consisting of 50 mg, 75 mg, 100 mg, 150 mg, 200 mg, 250 mg, 300 mg, 350 mg, 400 mg, 450 mg, and/or 500 mg. In some embodiments, the composition is in the form of a capsule or tablet and/or has a total weight of about 240 mg.

In some embodiments, the composition is in the form of a capsule or tablet and the dosage form comprises from about 1 to about 50 mg of a compound disclosed herein, having a USP acceptance value for content uniformity of less than about 15.

In some embodiments, a compound disclosed herein is administered as an aqueous suspension. In some embodiments, an aqueous suspension comprises a sweetening or flavoring agent, coloring matters or dyes and, if desired, emulsifying agents or suspending agents, together with diluents water, ethanol, propylene glycol, glycerin, or combinations thereof. In some embodiments, an aqueous suspension comprises a suspending agent. In some embodiments, an aqueous suspension comprises sodium carboxymethylcellulose, methylcellulose, hydroxypropylmethyl-cellulose, sodium alginate, polyvinyl-pyrrolidone, gum tragacanth and/or gum acacia. In some embodiments, an aqueous suspension comprises a dispersing or wetting agent. In some embodiments, an aqueous suspension comprises a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. In some embodiments, an aqueous suspension comprises a preservative. In some embodiments, an aqueous suspension comprises ethyl, or n-propyl p-hydroxybenzoate. In some embodiments, an aqueous suspension comprises a sweetening agent. In some embodiments, an aqueous suspension comprises sucrose, saccharin or aspartame.

In some embodiments, a compound disclosed herein is administered as an oily suspension. In some embodiments, an oily suspension is formulated by suspending the active ingredient in a vegetable oil (e.g., arachis oil, olive oil, sesame oil or coconut oil), or in mineral oil (e.g., liquid paraffin). In some embodiments, an oily suspension comprises a thickening agent (e.g., beeswax, hard paraffin or cetyl alcohol). In some embodiments, an oily suspension comprises sweetening agents (e.g., those set forth abovE). In some embodiments, an oily suspension comprises an anti-oxidant (e.g., butylated hydroxyanisol or alpha-tocopherol).

In some embodiments, a composition disclosed herein is formulated for parenteral injection (e.g., via injection or infusion, including intraarterial, intracardiac, intradermal, intraduodenal, intramedullary, intramuscular, intraosseous, intraperitoneal, intrathecal, intravascular, intravenous, intravitreal, epidural and/or subcutaneous). In some embodiments, a composition disclosed herein is administered as a sterile solution, suspension or emulsion.

In some embodiments, a formulation for parenteral administration includes aqueous and/or non-aqueous (oily) sterile injection solutions of the active compounds which may contain antioxidants, buffers, bacteriostats and/or solutes which render the formulation isotonic with the blood of the intended recipient; and/or aqueous and/or non-aqueous sterile suspensions which may include a suspending agent and/or a thickening agent. In some embodiments, a formulation for parenteral administration includes suitable stabilizers or agents which increase the solubility of the compounds to allow for the preparation of highly concentrated solutions.

In some embodiments, a compound disclosed herein is administered as an aqueous suspension. In some embodiments, an aqueous suspension comprises water, Ringer's solution and/or isotonic sodium chloride solution.

In some embodiments, a compound disclosed herein is administered as an oil-in-water microemulsion where the active ingredient is dissolved in the oily phase. In some embodiments, a compound disclosed herein is dissolved in a fatty oil (e.g., sesame oil, or synthetic fatty acid esters, (e.g., ethyl oleate or triglycerides, or liposomes. In some embodiments, a compound disclosed herein is dissolved in a mixture of soybean oil andrlecithin. In some embodiments, the oil solution is introduced into a water and glycerol mixture and processed to form a microemulsion.

In some embodiments, a composition formulated for parenteral administration is administered as a single bolus shot. In some embodiments, a composition formulated for parenteral administration is administered via a continuous intravenous delivery device (e.g., Deltec CADD-PLUS™ model 5400 intravenous pump).

In some embodiments, a formulation for injection is presented in unit dosage form, e.g., in ampoules or in multi-dose containers, with an added preservative. In some embodiments, a formulation for injection is stored in powder form or in a freeze-dried (lyophilized) condition requiring only the addition of the sterile liquid carrier, for example, saline or sterile pyrogen-free water, immediately prior to use.

In some embodiments, a formulation disclosed herein is administered by depot preparation. In some embodiments, a depot preparation is administered by implantation (for example subcutaneously or intramuscularly) or by intramuscular injection.

In some embodiments, a composition disclosed herein is formulated for topical administration. As used herein, topical administration means application of a composition such that the compound does not significantly enter the blood stream. In some embodiments, a composition disclosed herein is applied to the epidermis, the buccal cavity, the ear, eye and/or nose.

In some embodiments, a composition formulated for topical administration is formulated as a gel, liniment, lotion, cream, ointment or paste, solution, suspension, emulsion, or powder. In some embodiments, a composition disclosed herein is administered as an ointment or cream. In some embodiments, a composition disclosed herein is administered as a mouth wash. In some embodiments, a composition disclosed herein is administered via inhalation.

In some embodiments, a composition formulated for administration via inhalation is delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit is determined by providing a valve to deliver a metered amount. Alternatively, for administration by inhalation or insufflation, pharmaceutical preparations may take the form of a dry powder composition, for example a powder mix of the compound and a suitable powder base such as lactose or starch. The powder composition is presented in unit dosage form, in for example, capsules, cartridges, gelatin or blister packs from which the powder is administered with the aid of an inhalator or insufflator. For buccal or sublingual administration, the compositions may take the form of tablets, lozenges, pastilles, or gels formulated in conventional manner. Such compositions may comprise the active ingredient in a flavored basis such as sucrose and acacia or tragacanth.

In some embodiments, a composition disclosed herein is formulated for rectal administration. In some embodiments, a composition disclosed herein is administered as a suppository. In some embodiments, a composition suitable for rectal administration is prepared by mixing a compound disclosed herein with a suitable non-irritating excipient which is solid at ordinary temperatures but liquid at the rectal temperature and will therefore melt in the rectum to release the drug. In some embodiments, a composition suitable for rectal administration is prepared by mixing a compound disclosed herein with cocoa butter, glycerinated gelatin, hydrogenated vegetable oils, mixtures of polyethylene glycols of various molecular weights or fatty acid esters of polyethylene glycol.

For methods of preparing various pharmaceutical compositions see Remington's Pharmaceutical Sciences, Mack Publishing Company, Ester, Pa., 18th Edition (1990).

In some embodiments, the dosage form releases at least 60 percent of the drug within 30 minutes using U.S. Pharmacopeia (USP) Apparatus II at 50 rpm with 1% sodium lauryl sulfate in water as the dissolution medium. In some embodiments, the dosage form releases about 60-100 percent of the drug within 30 minutes using U.S. Pharmacopeia (USP) Apparatus II at 50 rpm with 1% sodium lauryl sulfate in water as the dissolution medium. In some embodiments, the dosage form releases about 60-90 percent of the drug within 30 minutes using U.S. Pharmacopeia (USP) Apparatus II at 50 rpm with 1% sodium lauryl sulfate in water as the dissolution medium. In some embodiments, the dosage form releases about 60-80 percent of the drug within 30 minutes using U.S. Pharmacopeia (USP) Apparatus II at 50 rpm with 1% sodium lauryl sulfate in water as the dissolution medium.

Dosages

The amount of pharmaceutical compositions administered will firstly be dependent on the mammal being treated. In the instances where pharmaceutical compositions are administered to a human subject, the daily dosage will normally be determined by the prescribing physician with the dosage generally varying according to the age, sex, diet, weight, general health and response of the individual individual, the severity of the individual's symptoms, the precise indication or condition being treated, the severity of the indication or condition being treated, time of administration, route of administration, the disposition of the composition, rate of excretion, drug combination, and the discretion of the prescribing physician.

In some embodiments, the dosage is between about 0.001 to about 1000 mg/kg body weight/day. In some embodiments, the amount of compound disclosed herein is in the range of about 0.5 to about 50 mg/kg/day. In some embodiments, the amount of compound disclosed herein is about 0.001 to about 7 g/day. In some embodiments, the amount of compound disclosed herein is about 0.01 to about 7 g/day. In some embodiments, the amount of compound disclosed herein is about 0.02 to about 5 g/day. In some embodiments, the amount of compound disclosed herein is about 0.05 to about 2.5 g/day. In some embodiments, the amount of compound disclosed herein is about 0.1 to about 1 g/day.

In some embodiments, the amount of compound disclosed herein is administered in a single dose, once daily. In some embodiments, the amount of compound disclosed herein is administered in multiple doses, more than once per day. In some embodiments, the amount of compound disclosed herein is administered twice daily. In some embodiments, the amount of compound disclosed herein is administered three times per day. In some embodiments, the amount of compound disclosed herein is administered four times per day. In some embodiments, the amount of compound disclosed herein is administered more than four times per day.

In some instances, dosage levels below the lower limit of the aforesaid range is more than adequate, while in other cases still larger doses is employed without causing any harmful side effect, e.g. by dividing such larger doses into several small doses for administration throughout the day. The amount administered will vary depending on the particular $IC_{50}$ value of the compound used. In combinational applications in which the compound is not the sole therapy, it is possible to administer lesser amounts of compound and still have therapeutic or prophylactic effect.

V. Combination Therapies

In some embodiments, a compound disclosed herein is administered in combination with a second therapeutic agent. In some embodiments, a compound disclosed herein is administered in combination with surgery, and/or radiation therapy.

In some embodiments, the second therapeutic agent is selected from cytotoxic agents, anti-angiogenesis agents and/or anti-neoplastic agents. In some embodiments, the second therapeutic agent is selected from alkylating agents, antimetabolites, epidophyllotoxins; antineoplastic enzymes, topoisomerase inhibitors, procarbazines, mitoxantrones, platinum coordination complexes, biological response modifiers and growth inhibitors, hormonal/anti-hormonal therapeutic agents, haematopoietic growth factors, aromatase inhibitors, anti-estrogens, anti-androgens, corticosteroids, gonadorelin agonists, microtubule active agents, nitrosoureas, lipid or protein kinase targeting agents, IMiDs, protein or lipid phosphatase targeting agents, anti-angiogenic agents, Akt inhibitors, IGF-I inhibitors, FGF3 modulators, mTOR inhibitors, Smac mimetics, HDAC inhibitors, agents that induce cell differentiation, bradykinin I receptor antagonists, angiotensin II antagonists, cyclooxygenase inhibitors, heparanase inhibitors, lymphokine inhibitors, cytokine inhibitors, IKK inhibitors, P38MAPK inhibitors, HSP90 inhibitors, multlikinase inhibitors, bisphosphanate, rapamycin derivatives, anti-apoptotic pathway inhibitors, apoptotic pathway agonists, PPAR agonists, RAR agonists, inhibitors of Ras isoforms, telomerase inhibitors, protease inhibitors, metalloproteinase inhibitors, aminopeptidase inhibitors, SHIP activators—AQX-MN 100, Humax-CD20 (ofatumumab), CD20 antagonists, IL2-diptheria toxin fusions, or combinations thereof.

In some embodiments, the second therapeutic agent is selected from ARRY-797, dacarbazine (DTIC), actinomycins $C_2$, $C_3$, D, and $F_1$, cyclophosphamide, melphalan, estramustine, maytansinol, rifamycin, streptovaricin, doxorubicin, daunorubicin, epirubicin, idarubicin, detorubicin, carminomycin, idarubicin, epirubicin, esorubicin, mitoxantrone, bleomycins A, $A_2$, and B, camptothecin, Irinotecan, Topotecan, 9-am inocamptothecin, 10,11-methylenedioxycamptothecin, 9-nitrocamptothecin, bortezomib, temozolomide, TAS103, NPI0052, combretastatin, combretastatin A-2, combretastatin A-4, calicheamicins, neocarcinostatins, epothilones A B, C, and semi-synthetic variants, Herceptin, Rituxan, CD40 antibodies, asparaginase, interleukins, interferons, leuprolide, and pegaspargase, 5-fluorouracil, fluorodeoxyuridine, ptorafur, 5'-deoxyfluorouridine, UFT, MITC, S-1 capecitabine, diethylstilbestrol, tamoxifen, toremefine, tolmudex, thymitaq, flutamide, fluoxymesterone, bicalutamide, finasteride, estradiol, trioxifene, dexamethasone, leuproelin acetate, estramustine, droloxifene, medroxyprogesterone, megesterol acetate, aminoglutethimide, testolactone, testosterone, diethylstilbestrol, hydroxyprogesterone, mitomycins A, B and C, porfiromycin, cisplatin, carboplatin, oxaliplatin, tetraplatin, platinum-DACH, ormaplatin, thalidomide, lenalidomide, CI-973, telomestatin, CHIR258, Rad 001, SAHA, Tubacin, 17-AAG, sorafenib, JM-216, podophyllotoxin, epipodophyllotoxin, etoposide, teniposide, Tarceva, Iressa, Imatinib, Miltefosine, Perifosine, aminopterin, methotrexate, methopterin, dichloro-methotrexate, 6-mercaptopurine, thioguanine, azattuoprine, allopurinol, cladribine, fludarabine, pentostatin, 2-chloroadenosine, deoxycytidine, cytosine arabinoside, cytarabine, azacitidine, 5-azacytosine, gencitabine, 5-azacytosine-arabinoside, vincristine, vinblastine, vinorelbine, leurosine, leurosidine and vindesine, paclitaxel, taxotere and/or docetaxel.

In some embodiments, the second therapeutic agent is selected from corticosteroids, non-steroidal anti-inflammatories, muscle relaxants and combinations thereof with other agents, anaesthetics and combinations thereof with other agents, expectorants and combinations thereof with other agents, antidepressants, anticonvulsants and combinations thereof; antihypertensives, opioids, topical cannabinoids, capsaicin, betamethasone dipropionate (augmented and non-augemnted), betamethasone valerate, clobetasol propionate, prednisone, methyl prednisolone, diflorasone diacetate, halobetasol propionate, amcinonide, dexamethasone, dexosimethasone, fluocinolone acetononide, fluocinonide, halocinonide, clocortalone pivalate, dexosimetasone, flurandrenalide, salicylates, ibuprofen, ketoprofen, etodolac, diclofenac, meclofenamate sodium, naproxen, piroxicam, eelecoxib, cyclobenzaprine, baclofen, cyclobenzaprine/lidocaine, baclofen/cyclobenzaprine, cyclobenzaprine/lidocaine/ketoprofen, lidocaine, lidocaine/deoxy-D-glucose, prilocaine, EMLA Cream (Eutectic Mixture of Local Anesthetics (lidocaine 2.5% and prilocaine 2.5%), guaifenesin, guaifenesin/ketoprofen/cyclobenzaprine, amitryptiline, doxepin, desipramine, imipramine, amoxapine, clomipramine, nortriptyline, protriptyline, duloxetine, mirtazepine, nisoxetine, maprotiline, reboxetine, fluoxetine, fluvoxarnine, carbamazepine, felbamate, lamotrigine, topiramate, tiagabine, oxcarbazepine, carbamezipine, zonisamide, mexiletine, gabapentin/clonidine, gabapentin/carbamazepine, carbamazepine/cyclobenzaprine, antihypertensives including clonidine, codeine, loperarnide, tramadol, morphine, fentanyl, oxycodone, hydrocodone, levorphanol, butorphanol, menthol, oil of wintergreen, camphor, eucalyptus oil, turpentine oil; CB1CB2 ligands, acetaminophen, infliximab, nitric oxide synthase inhibitors, particularly inhibitors of inducible nitric oxide synthase, PDE4 inhibitors—similar mechanism to Ibudilast (AV-411), CDC-801, JNK inhibitors-CC-401, Combination TNF/PDE4 inhibitors CDC-998, IL1 antagonists e.g. Anakinra-Kineret, AMG 108, (mAb) that targets IL-1, SHIP activators—AQX-MN100, C5 antagonists, C5a inhibitors, Pexelizumab, Pyrimidine synthesis inhibitors, lymphokine inhibitors, cytokine inhibitors, IKK inhibitors, P38MAPK inhibitors, ARRY-797, HSP90 inhibitors, multlikinase inhibitors, bisphosphanates, PPAR agonists, Cox1 and cox 2 inhibitors, Anti-CD4 therapy, B-cell inhibitors, COX/LOX dual inhibitors, Immunosuppressive agents, iNOS inhibitors, NSAIDs, sPLA2 inhibitors, Colchicine, allopurinol, oxypurinol, Gold, Ridaura Auranofin, febuxostat, Puricase, PEG-uricase formulations, Benzbromarone, Long-acting beta-2 agonists (LABAs), salmeterol (Serevent Diskus) and formoterol (Foradil), Leukotriene modifiers include montelukast (Singulair) and zafirlukast (Accolate). Inhaled cromolyn (Intal) or nedoeromil (Tilade), Theophylline. Short-acting beta-2 agonists, Ipratropium (Atrovent), Immunotherapy-(Allergy-desensitization shots), Anti-IgE monoclonal antibodies—Xolair, Common DMARDs include hydroxychloroquine (Plaquenil), the gold compound auranofin (Ridaura), sulfasalazine (Azulfidine), minocycline (Dynacin, Minocin) and methotrexate (Rheumatrex), leflunomide (Arava), azathioprine (Imuran), cyclosporine (Neoral, Sandimmune) and cyclophosphamide (Cytoxan), Antibiotics, CD80 antagonists, costimulatory factor antagonists, Humax-CD20 (ofatumumab); CD20 antagonists, MEK inhibitors, NF kappa B inhibitors, anti B-cell antibodies, denosumab, mAb that specifically targets the receptor activator of nuclear factor kappa B ligand (RANKL). IL17 inactivating anti-bodies, IL-17 receptor antagonists/inhibitors, CTLA inhibitors, CD20 inhibitors, soluble VEGFR-1 receptors, anti-VEGFR-1 receptor antibodies, anti-VEGF antibodies, integrin receptor antagonist, Selectin inhibitors, P-selectin and E-selectin inhibitors, Phospholipase A2 Inhibitors, Lipoxygenase Inhibitors, RANKL and RANK antagonists/antibodies, Osteoprotegerin antagonists, Lymphotoxin inhibitors, B-lymphocyte stimulator, MCP-1 inhibitors, MIF inhibitors, inhibitors of: CD2, CD3, CD4, CD25, CD40 and CD40 Ligand CD152 (CTLA4), Macrolide immunosuppressants, Selective inhibitors of nucleotide metabolism, Inhibitors of chemotaxis, CXC receptor and CXC ligand inhibitors, Chemokine Antagonists, leukocyte chemotaxis inhibitors Adhesion Molecule blockers, Selectins Lymphocyte Function Antigen-I (LFA-1, CD11a) antagonists, Very Late Antigen-4 (VLA-4) antagonists, Matrix Metalloprotease Inhibitors, Elastase Inhibitors, Cathepsin Inhibitors, or combinations thereof.

In some embodiments, the second therapeutic agent is selected from beta-blockers, carbonic anhydrase inhibitors, .alpha.- and .beta.-adrenergic antagonists including al-adrenergic antagonists, .alpha.2 agonists, miotics, prostaglandin analogs, corticosteroids, and/or immunosuppressant agents.

In some embodiments, the second therapeutic agent is selected from timolol, betaxolol, levobetaxolol, carteolol, levobunolol, propranolol, brinzolarnide, dorzolamide, nipradilol, Iopidine, brimonidine, pilocarpine, epinephrine, latanoprost, travoprost, bimatoprost, unoprostone, dexamethasone, prednisone, methylprednisolone, azathioprine, cyclosporine, and/or immunoglobulins.

In some embodiments, the second therapeutic agent is selected from corticosteroids, immunosuppressants, prostaglandin analogs and/or antimetabolites. In some embodiments, the second therapeutic agent is selected from dexamethasone, prednisone, methylprednisolone, azathioprine, cyclosporine, immunoglobulins, latanoprost, travoprost, bimatoprost, unoprostone, infliximab, rutuximab, methotrexate, non-steroidal anti-inflammatories, muscle relaxants and combinations thereof with other agents, anaesthetics and combinations thereof with other agents, expectorants and combinations thereof with other agents, antidepressants, anticonvulsants and combinations thereof; antihypertensives, opioids, topical cannabinoids, and other agents, such as capsaicin, betamethasone dipropionate (augmented and nonaugemnted), betamethasone valerate, clobetasol propionate, prednisone, methyl prednisolone, diflorasone diacetate, halobetasol propionate, amcinonide, dexamethasone, dexosimethasone, fluocinolone acetononide, fluocinonide, halocinonide, clocortalone pivalate, dexosimetasone, flurandrenalide, salicylates, ibuprofen, ketoprofen, etodolac, diclofenac, meclofenamate sodium, naproxen, piroxicam, celecoxib, cyclobenzaprine, baclofen, cyclobenzaprine/lidocaine, baclofen/cyclobenzaprine, cyclobenzaprine/lidocaine/ketoprofen, lidocaine, lidocaine/deoxy-D-glucose, prilocaine, EMLA Cream (Eutectic Mixture of Local Anesthetics (lidocaine 2.5% and prilocaine 2.5%), guaifenesin, guaifenesin/ketoprofen/cyclobenzaprine, amitryptiline, doxepin, desipramine, imipramine, amoxapine, clomipramine, nortriptyline, protriptyline, duloxetine, mirtazepine, nisoxetine, maprotiline, reboxetine, fluoxetine, fluvoxamine, carbamazepine, felbamate, lamotrigine, topiramate, tiagabine, oxcarbazepine, carbamezipine, zonisamide, mexiletine, gabapentin/clonidine, gabapentin/carbamazepine, carbamazepine/cyclobenzaprine, antihypertensives including clonidine, codeine, loperamide, tramadol, morphine, fentanyl, oxycodone, hydrocodone, levorphanol, butorphanol, menthol, oil of wintergreen, camphor, eucalyptus oil, turpentine oil; CB1/CB2 ligands, acetaminophen, infliximab; nitric oxide synthase inhibitors, particularly inhibitors of inducible nitric oxide synthase; and other agents, such as capsaicin. PDE4 inhibitors—similar mechanism to Ibudilast (AV-411), CDC-801, JNK inhibitors CC-401, Combination TNF/PDE4 inhibitors—CDC-998, IL1 antagonists e.g. Anakinra-Kineret, AMG 108, (mAb) that targets IL-1, SHIP activators—AQX-MN100, C5 antagonists, C5a inhibitors, Pexelizumab, Pyrimidine synthesis inhibitors, lymphokine inhibitors, cytokine inhibitors, IKK inhibitors, P38MAPK inhibitors, ARRY-797, HSP90 inhibitors, multlikinase inhibitors, bisphosphanates, PPAR agonists, Cox 1 and cox 2 inhibitors, Anti-CD4 therapy, B-cell inhibitors, COX/LOX dual inhibitors, Immunosuppressive agents, iNOS inhibitors, NSAIDs, sPLA2 inhibitors, Colchicine, allopurinol, oxypurinol, Gold, Ridaura Auranofin, febuxostat, Puricase, PEG-uricase formulations, Benzbromarone, Long-acting beta-2 agonists (LABAs), salmeterol (Serevent Diskus) and formoterol (Foradil), Leukotriene modifiers include montelukast (Singulair) and zafirlukast (Accolate). Inhaled cromolyn (Intal) or nedocromil (Tilade), Theophylline. Short-acting beta-2 agonists, Ipratropium (Atrovent), Immunotherapy-(Allergy-desensitization shots), Anti-IgE monoclonal antibodies—Xolair, Common DMARDs include hydroxychloroquine (Plaquenil), the gold compound auranofin (Ridaura), sulfasalazine (Azulfidine), minocycline (Dynacin, Minocin) and methotrexate (Rheumatrex), leflunomide (Arava), azathioprine (Imuran), cyclosporine (Neoral, Sandimmune) and cyclophosphamide (Cytoxan), Antibiotics, CD80 antagonists, costimulatory factor antagonists, Humax-CD20 (ofatumumab); CD20 antagonists, MEK inhibitors, NF kappa B inhibitors, anti B-cell antibodies, denosumab, mAb that specifically targets the receptor activator of nuclear factor kappa B ligand (RANKL). IL17 inactivating anti-bodies, IL-17 receptor antagonists/inhibitors, CTLA inhibitors, CD20 inhibitors, soluble VEGFR-1 receptors, anti-VEGFR-1 receptor antibodies, anti-VEGF antibodies, integrin receptor antagonist, Selectin inhibitors, P-selectin and E-selectin inhibitors, Phospholipase A2 Inhibitors, Lipoxygenase Inhibitors, RANKL and RANK antagonists/antibodies, Osteoprotegerin antagonists, Lymphotoxin inhibitors, B-lymphocyte stimulator, MCP-1 inhibitors, MIF inhibitors, inhibitors of: CD2, CD3, CD4, CD25, CD40 and CD40 Ligand CD152 (CTLA4), Macrolide immunosuppressants, Selective inhibitors of nucleotide metabolism, Inhibitors of chemotaxis, CXC receptor and CXC ligand inhibitors, Chemokine Antagonists, leukocyte chemotaxis inhibitors Adhesion Molecule blockers, Selectins Lymphocyte Function Antigen-1 (LFA-1, CD11a) antagonists, Very Late Antigen-4 (VLA-4) antagonists, Matrix Metalloprotease Inhibitors, Elastase Inhibitors, Cathepsin Inhibitors, or combinations thereof.

In some embodiments, the second therapeutic agent is selected from insulin, insulin derivatives and mimetics, insulin secretagogues, insulin sensitizers, biguanide agents, alpha-glucosidase inhibitors, insulinotropic sulfonylurea receptor ligands, protein tyrosine phosphatase-113 (PTP-1B) inhibitors, GSK3 (glycogen synthase kinase-3) inhibitors, GLP-1 (glucagon like peptide-1), GLP-1 analogs, DPPIV (dipeptidyl peptidase IV) inhibitors, RXR ligands sodium-dependent glucose co-transporter inhibitors, glycogen phosphorylase A inhibitors, an AGE breaker, PPAR modulators, LXR and FXR modulators, non-glitazone type PPARS agonist, selective glucocorticoid antagonists, metformin, Glipizide, glyburide, Amaryl, meglitinides, nateglinide, repaglinide, PT-112, SB-517955, SB4195052, SB-216763, NN-57-05441, NN-57-05445, GW-0791, AGN-.sup.194.sup.204, T-1095, BAY R3401, acarbose Exendin-4, DPP728, LAF237, vildagliptin, MK-0431, saxagliptin, GSK23A, pioglitazone, rosiglitazone, (R)-1-{4-[5-methyl-2-(4-trifluoromethyl-phenyl)-oxazol-4-ylmethoxy]-benze-nesulfonyl}2,3-dihydro-1H-indole-2-carboxylic acid described in the patent application WO 03/043985, as compound 19 of Example 4, and/or GI-262570.

Kits

The compounds, compositions and/or methods described herein provide kits for the treatment of disorders, (e.g., the ones described herein). These kits comprise a compound, compounds or compositions described herein in a container and, optionally, instructions teaching the use of the kit according to the various methods and/or approaches described herein. Such kits may also include information, (e.g., scientific literature references, package insert materials, clinical trial results, and/or summaries of these and/or the like), which indicate or establish the activities and/or advantages of the composition, and/or which describe dosing, administration, side effects, drug interactions, or other information useful to the health care provider. Such information is based on the results of various studies, for example, studies using experimental animals involving in vivo models and/or studies based on human clinical trials. Kits described herein is provided, marketed and/or promoted to health providers, including physicians, nurses, pharmacists, formulary officials, and/or the like. Kits may also, in some embodiments, be marketed directly to the consumer.

EXAMPLES

Example 1

Preparation of N-(3.4-difluoro-2-(2-fluoro-4-iodophenylamino)phenyl)-1-(2,3-dihydroxypropyl)cyclopropane-1-sulfonamide N-(3.4-difluoro-2-(2-fluoro-4-iodophenylamino)phenyl)-1-(2,3-dihydroxypropyl)cyclopropane-1-sulfonamide was prepared according to previously described procedures (see published international patent application WO 2007/014011) and as outlined below.

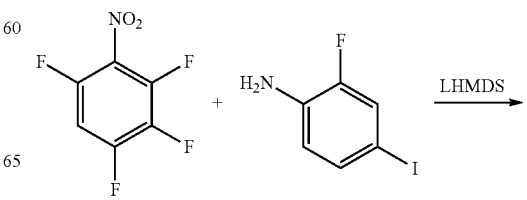

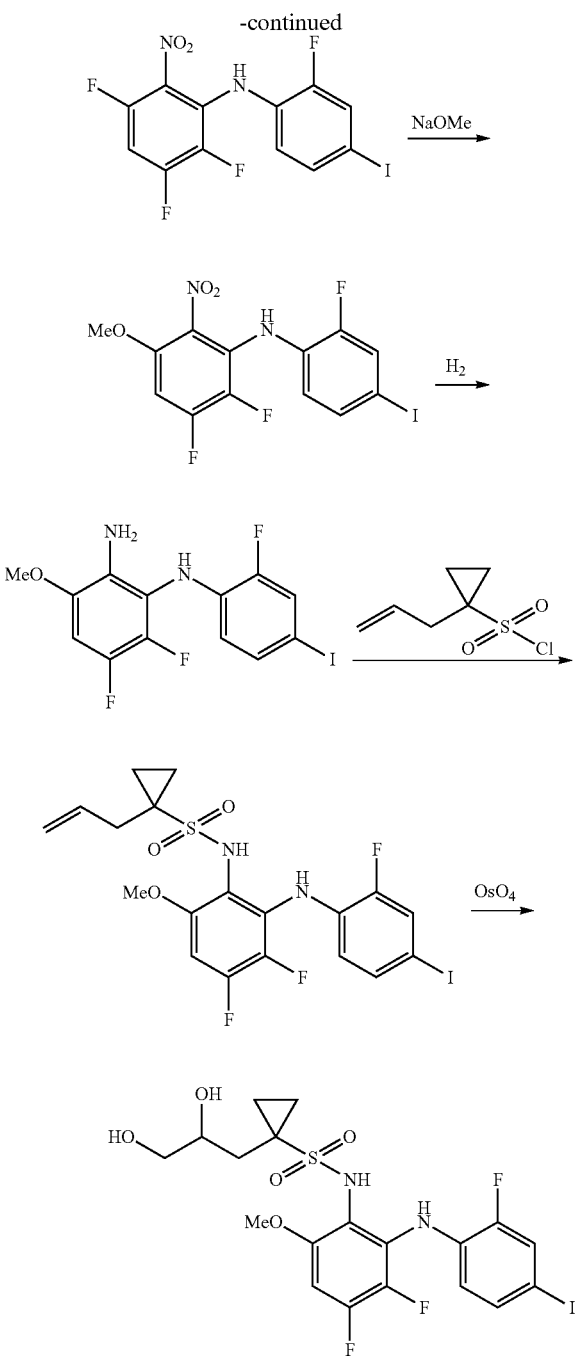

Step A: 2-Fluoro-N-(2,3,5-trifluoro-6-nitrophenyl)-4-iodobenzenamine

A solution of 1.0 M lithium hexa methyl disilazide (LiN(SiMe$_3$)$_2$) "LHMDS" (15.37 mL, 15.37 mmol) was slowly added to a stirred solution of 2-fluoro-4-iodoaniline (3.64 g, 15.37 mmol) in dry THF (100 mL) under nitrogen at −78° C. and stirring continued at −78° C. for another hour. 2,3,4,6-Tetrafluoronitrobenzene was added, and the reaction mixture was allowed to warm to room temperature and stirring continued for another 16 hours. Ethyl acetate (200 mL) was added and the organic phase was washed with water, dried over sodium sulfate and further purified by column chromatography to provide the product as a yellow solid (3.75 g, 59.24%). M−H$^+$: 410.9. $^1$H NMR (DMSO, 300 MHz): 6.85 (t, 1H); 7.38 (d, 1H); 7.62 (m, 2H); 8.78 (s, 1H).

Step B: 2-Fluoro-N-(2,3-difluaro-5-methoxy-6-nitrophenyl)-4-iodobenzenamine

A stirred solution of (2-fluoro-4-iodo-phenyl)-(2,3,5-trifluoro-6-nitro-phenyl)-amine (1.23 g, 3 mmol) in dry THF (25 ml) under nitrogen was cooled to −78° C. and a solution of 25% sodium methoxide (0.68 ml, 0.3 mmol) was added slowly. The reaction mixture was allowed to warm to room temperature and stirring continued for another 16 hours. TLC indicated incomplete reaction. Ethyl acetate (100 mL) was added to the reaction mixture and the organic layer was washed with water, dried over sodium sulfate and further purified by column chromatography to provide the desired compound as a yellow solid (0.6 g, 47.6%). m/z=424 [M+H]$^+$.

Step C: 5,6-Difluoro-N$^1$-(2-fluoro-4-iodophenyl)-3-methoxybenzene-1,2-diamine

Ammonium chloride (1.18 g, 20.16 mmol) and iron powder (1.15 g, 21.44 mmol) were added to a stirred solution of (2,3-difluoro-5-methoxy-6-nitro-phenyl)-(2-fluoro-4-iodo-phenyl)-amine (0.57 g, 1.34 mmol) in ethanol (20 mL). The mixture was stirred at reflux for 16 hours, cooled to room temperature, filtered over celite and the filtrate concentrated to dryness. The resulting residue was taken into ethyl acetate, washed with water, dried over sodium sulfate and further purified by crystallization from ethanol to provide the product as an off-white solid (0.47 g, 90.3%). M−H$^+$: 393.2. $^1$H NMR (DMSO, 300 MHz): 3.76 (s, 3H); 6.1 (t, 1H); 6.8-7.0 (m, 1H); 7.2 (d, 1H); 7.35 (s, 1H); 7.42 (d, 1H).

Step D: 1-Allyl-N-(3,4-difluoro-2-(2-fluoro-4-iodophenylamino)-6-methoxyphenyl)cyclopropane-1-sulfonamide To a stirred solution of 5,6-difluoro-N$^1$-(2-fluoro-4-iodophenyl)-3-methoxybenzene-1,2-diamine (1 eq) in anhydrous pyridine (5 ml/mmole) was added 1-allyl-cyclopropanesulfonyl chloride (1-5 eq). The reaction mixture was stirred at 40° C. for 48 hours. The reaction mixture was partitioned with water and ethyl acetate. The organic layer was washed with brine, dried (MgSO$_4$) and concentrated under reduced pressure. The residue was purified by flash column chromatography on silica to obtain the title product. $^1$H NMR (CDCl$_3$, 300 MHz): δ 7.417 (dd, 1H), 7.309 (s, 1H), 7.25 (m, 1H), 6.89 (m, 1H), 6.52 (m, 1H), 6.427 (m, 1H), 6.03 (s, 1H), 5.668 (m, 1H), 5.11 (t, 1H), 3.9 (s, 3H), 2.75 (d, 2H), 1.21 (m, 2H), 0.767 (m, 2H).

Step E: N-(3,4-difluoro-2-(2-fluoro-4-iodophenylamino)-6-methoxyphenyl)-1-(2,3-dihydroxypropyl) cyclopropane-1-sulfonamide 1-Allyl-N-(3,4-difluoro-2-(2-fluoro-4-iodophenylamino)-6-methoxyphenyl) cyclopropane-1-sulfonamide (97 mg, 0.18 mmol) and 4-methylmorpholine N-oxide (21 mg, 0.18 mmol) were dissolved in THF (8 mL). Osmium tetroxide was added at room temperature (0.018 mmol, 0.13 mL, 4% in H$_2$O) and the reaction mixture was stirred at room temperature for 16 hours. Ethyl acetate was added, and the organic phase was washed with water, dried (MgSO$_4$) and concentrated under reduced pressure. The residue was purified over silica gel chromatography (eluants: EtOAc/MeOH) to obtain the titled product (0.80 g, 78%). $^1$H NMR (CDCl$_3$, 300 MHz): δ7.38 (dd, J=1.7 & 10.3 Hz, 1H), 7.26 (m, 1H), 7.14 (s, 1H), 6.87 (s, 1H), 6.53 (dd, J=6.8 & 11.4 Hz, 1H), 6.43 (m, 1H), 4.06 (in, 1H), 3.89 (s, 3H), 3.63 (dd, J=3.7 & 11.1 Hz, 1H), 3.49 (dd, J=6.4 & 11.1 Hz, 1H), 2.3 (dd, J=9.7 & 16.1 Hz, 1H), 1.77 (dd, J=1.9 & 16.0 Hz, 1H), 1.37 (m, 1H), 1.25 (m, 1H), 1.21 (m, 2H), 0.86 (m, 2H); m/z=571 [M−1].

Example 2

Preparation of N—(S)-(3,4-difluoro-2-(2-fluoro-4-iodophenylarnino)-6-methoxyphenyl)-1-(2,3-dihydroxypropyl)cyclopropane-1-sulfonamide

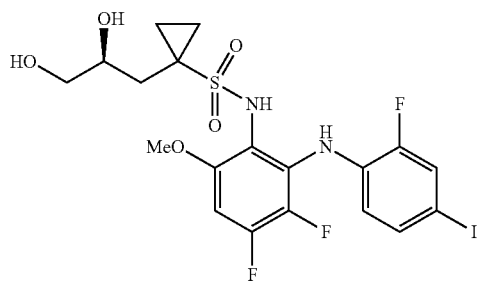

The pure S isomer was obtained by chiral HPLC separation of the racemic mixture. $^1$H NMR (CDCl$_3$, 300 MHz): δ 7.38 (dd, J=1.7 & 10.3 Hz, 1H), 7.26 (m, 1H), 7.14 (s, 1H), 6.87 (s, 1H), 6.53 (dd, J=6.8 & 11.4 Hz, 1H), 6.43 (m, 1H), 4.06 (m, 1H), 3.89 (s, 3H), 3.63 (dd, J=3.7 & 11.1 Hz, 1H), 3.49 (dd, J=6.4 & 11.1 Hz, 1H), 2.3 (dd, J=9.7 & 16.1 Hz, 1H), 1.77 (dd, J=1.9 & 16.0 Hz, 1H), 1.37 (n, 1H), 1.25 (m, 1H), 1.21 (m, 2H), 0.86 (m, 2H); m/z=571 [M-1]$^-$.

Example 3

Preparation of N—(R)-(3,4-difluoro-2-(2-fluoro-4-iodophenylamino)-6-methoxyphenyl)-1-(2,3-dihydroxypropyl) cyclopropane-1-sulfonamide

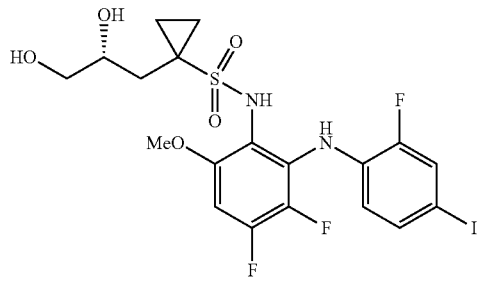

The pure R isomer was obtained by chiral HPLC separation of the racemic mixture. $^1$H NMR (CDCl$_3$, 300 MHz): δ7.38 (dd, J=1.7 & 10.3 Hz, 1H), 7.26 (m, 1H), 7.14 (s, 1H), 6.87 (s, 1H), 6.53 (dd, J=6.8 & 11.4 Hz, 1H), 6.43 (m, 1H), 4.06 (m, 1H), 3.89 (s, 31-1), 3.63 (dd, J=3.7 & 11.1 Hz, 1H), 3.49 (dd, J=6.4 & 11.1 Hz, 1H), 2.3 (dd, J=9.7 & 16.1 Hz, 1H), 1.77 (dd, J=1.9 & 16.0 Hz, 1H), 1.37 (m, 1H), 1.25 (m, 1H), 1.21 (m, 2H), 0.86 (m, 2H); m/z=571 [M-1]$^-$.

Example 4

Preparation of crystalline polymorph Form A of N—(S)-(3,4-difluoro-2-(2-fluoro-4-iodophenylamino)-6-methoxyphenyl)-1-(2,3-dihydroxypropyl) cyclopropane-1-sulfonamide Preparation i) N—(S)-(3,4-difluoro-2-(2-fluoro-4-iodophenylamino)-6-methoxyphenyl)-1-(2,3-dihydroxypropyl) cyclopropane-1-sulfonamide (216.10 g) was charged to a 4 L Erlenmeyer flask equipped with a large magnetic stir bar and a magnetic stirrer/hot plate. Ethyl Acetate (ca. 600 mL, purchased from Fisher) was added. Heating and stirring were initiated to form a brown suspension. The mixture was brought to a low reflux and additional ethyl acetate (ca. 200 mL) was added to effect complete dissolution giving a dark brown solution. Heptane (purchased from Acros) was slowly added portionwise to the refluxing solution at a rate that all precipitates that formed on each addition were quickly dissolved and reflux maintained. Upon the addition of 2 L of heptanes to the solution the solids formed dissolved very slowly at reflux. Heating was stopped and the crystallization mixture allowed to equilibrate to room temperature with stirring over 16 h. A thick layer of crystalline material developed around the surface of the glass over the aging period. The resulting suspension was equilibrated in an ice/water bath with stirring. The suspension was filtered on a 25 cm Buchner funnel dressed with Whatman #1 filter media. The collected crystals were washed with heptanes (1 L) and allowed to air dry under vacuum, The crystals were further dried at 40° C./<1 torr over 20 h to yield the product as a pink crystalline solid (160.99 g, 77.2%).

Preparation ii) N—(S)-(3,4-difluoro-2-(2-fluoro-4-iodophenylamino)-6-methoxyphenyl)-1-(2,3-dihydroxypropyl) cyclopropane-1-sulfonamide (13.2 g) and ethyl acetate (30 mL) were charged to an Erlenmeyer flask equipped with a large magnetic stir bar and a magnetic stirrer/hot plate. Stirring and heating to low reflux were initiated to effect complete dissolution giving a dark brown solution. Heptanes were slowly added portionwise to the refluxing solution at a rate that all precipitates that formed on each addition were quickly dissolved and reflux maintained, until the addition of heptanes to the solution caused the solids formed to dissolve very slowly at reflux (~90 mL heptanes). Heating was stopped and the crystallization mixture allowed to equilibrate to room temperature with stirring over 16 h, A thick layer of crystalline material developed around the surface of the glass over the aging period. The resulting suspension was equilibrated in an ice/water bath with stirring. The suspension was filtered on Buchner funnel dressed with Whatman #1 filter media. The collected crystals were washed with heptanes, and allowed to air dry under vacuum. The crystals were further dried at 40° C./<1 torr over 20 h to yield the product as a pink crystalline solid.

Preparation iii) N—(S)-(3,4-difluoro-2-(2-fluoro-4-iodophenylamino)-6-methoxyphenyl)-1-(2,3-dihydroxypropyl) cyclopropane-1-sulfonamide (44.8 g) and ethyl acetate (750 mL) were charged to an Erlenmeyer flask equipped with a large magnetic stir bar and a magnetic stirrer/hot plate. Stirring and heating to low reflux were initiated to effect complete dissolution giving a dark brown solution. Hexanes were slowly added portionwise to the refluxing solution at a rate that all precipitates that formed on each addition were quickly dissolved and reflux maintained, until the addition of hexanes to the solution caused the solids formed to dissolve very slowly at reflux (~2 L hexanes), Heating was stopped and the crystallization mixture allowed to equilibrate to room temperature with stirring over 16 h. A thick layer of crystalline material developed around the surface of the glass over the aging period. The resulting suspension was equilibrated in an ice/water bath with stirring. The suspension was filtered on Buchner funnel dressed with Whatman #1 filter media. The collected crystals were washed, and allowed to air dry under vacuum. The crystals were further dried at 40° C./<1 torr over 20 h to yield the product as a pink crystalline solid.

Example 5

Preparation of crystalline polymorph of N—(R)-(3,4-difluoro-2-(2-fluoro-4-iodophenylamino)-6-methoxyphenyl)-1-(2,3-dihydroxypropyl)cyclopropane-1-sulfonamide N—(R)-(3,4-difluoro-2-(2-fluoro-4-iodophenylamino)-6-methoxyphenyl)-1-(2,3-dihydroxypropyl) cyclopropane-1-sulfonamide (216.10 g) is charged to a 4 L Erlenmeyer flask equipped with a large magnetic stir bar and a magnetic stirrer/hot plate. Ethyl Acetate (ca. 600 mL) is added. Heating and stirring are initiated to form a brown suspension. The mixture is brought to a low reflux and additional ethyl acetate (ca. 200 mL) is added to effect complete dissolution giving a dark brown solution. Heptane is charged to the solution slowly portionwise to the refluxing solution at a rate that all precipitates that form on each addition are quickly dissolved and reflux is maintained. Upon the addition of 2 L of heptanes to the solution the solids formed dissolve very slowly at reflux. Heating is stopped and the crystallization mixture is allowed to equilibrate to room temperature with stirring over 16 h. A thick layer of crystalline material develops around the surface of the glass over the aging period. The resulting suspension is equilibrated in an ice/water bath with stirring. The suspension is filtered on a 25 cm Buchner funnel dressed with Whatman #1 filter media. The collected crystals are washed with heptanes (1 L) and allowed to air dry under vacuum. The crystals are further dried at 40° C./<1 torr over 20 h.

Example 6

Generation of IC50 Data

Materials and preparation of reagents: Human GST-MEK1 and the constitutively active allele GST-MEK1$^{CA}$ (harboring the mutations Ser218Asp and Ser222Asp) were subcloned into the yeast expression vector pGEM4Z (Promega, Madison, Wis.) from the wild type human MEK1 cDNA. GST-MEK1$^{CA}$ was expressed in *Escherichia coil* and partially purified using Glutathione Sepharose 4B affinity resin (Amersham Pharmacia Biotech, Piscataway, N.J.). The ERK2 allele was subcloned from MAPK2/Erk2 cDNA (wild type) in pUSEamp (Upstate Biotechnology, Inc., Waltham, Mass.) into the vector pET21a (Novagen, Madison, Wis.) resulting in an N-terminal histidine-tagged mouse ERK2 allele. ERK2 was expressed and purified to homogeneity [Zhang, 1993 #33]. Myelin basic protein (MBP) was purchased from Gibco BRL (Rockville, Md.). EasyTides adenosine 5'-triphosphate (ATP) ([γ-$^{33}$P]) (NEN Perkin Elmer, Wellesley, Mass.) was the source of radiolabel for all kinase reactions. Activated Raf-1 (truncated) and activated MAPKinase 2/ERK2 were purchased from Upstate, Inc. (Lake Placid, N.Y.). 4-20% Criterion Precast gels were purchased from Bio-Rad (Hercules, Calif.).

Determination of enzymatic activity: Compounds were diluted from dimethylsulfoxide (DMSO) stocks into 1xHMNDE (20 mM. HEPES pH 7.2, 1 mM MgCl$_2$, 100 mM NaCl, 1.25 mM DTT, 0.2 mM EDTA). A typical 25-microliter assay contained 0.002 nanomoles MEK1$^{CA}$, 0.02 nanomoles ERK2, 0.25 nanomoles MBP, 0.25 nanomoles unlabeled ATP, and 0.1 µCi [γ$^{33}$P] ATP. The screening assay essentially comprised four additions. Five µl of diluted compound were dispensed to 96-well assay plates. Ten µl of 2.5x enzyme cocktail (MEK1$^{CA}$ and ERK2 only) were then added to each well followed by a pre-incubation for 30 minutes at ambient temperature. Ten µl of 2.5x substrate cocktail (labeled and unlabeled ATP plus MBP) were then added, followed by incubation for 60 minutes at ambient temperature. Finally, 100 µl of 10% trichloroacetic acid (TCA) were added and incubated for 30 minutes at room temperature to halt the reaction and precipitate radiolabeled protein products. Reaction products were harvested on glass fiber 96 well filter plates prewetted with water and 1% pyrophosphate. The filter plate was then washed 5 times with water. Water was displaced by absolute ethanol and the plate was allowed to air dry for 30 minutes at room temperature. A back seal was applied manually and 40 µl of scintillation cocktail were dispensed to each well. A top seal was applied and the plate was counted in the TopCount for two seconds per well. For certain experiments a truncated version of MEK that requires activation by Raf kinase were used.

Example 7

Generation of EC50 Data

Effects of compounds in the cell were determined by Western blotting for phosphorylated ERK. MDA-MB-231 breast cancer cells were plated in a 48 well plate at 20,000 cells per well and grown in a 37° humidified CO$_2$ incubator. The following day, the growth media (DMEM+10% fetal bovine serum) was removed and replaced with starve media (DMEM+0.1% fetal bovine serum). Cells were incubated in the starve media for sixteen hours and then treated with a range of compound concentrations for thirty minutes. After incubation with compound, cells were stimulated with 100 ng/ml EGF for five minutes. The cells were then lysed and analyzed by Western blot using a monoclonal antibody raised to phosphorylated ERK. The signal was amplified using a secondary antibody conjugated to a near-IR dye and detected on a Licor Odyssey scanner. The intensity of signal was quantitated and this data was used to generate dose response curves and EC50 calculations.

Example 8

Activity Data of Compounds

The compounds described in examples 1, 2 and 3 were tested in the assays described above. The results are summarized in the table below (A, EC$_{50}$=<2.0 nM; B, EC$_{50}$=2.0-15 nM):

| Compound Number | Structure | Activity |
|---|---|---|
| Eg. 1 (Racemic) | 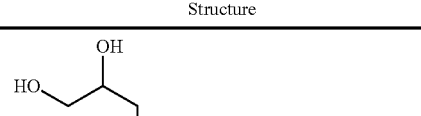 | A |

-continued

| Compound Number | Structure | Activity |
|---|---|---|
| Eg. 2 (S isomer) | [chemical structure: (S)-N-(3,4-difluoro-2-(2-fluoro-4-iodophenylamino)-6-methoxyphenyl)-1-(2,3-dihydroxypropyl)cyclopropane-1-sulfonamide] | A |
| Eg. 3 (R isomer) | [chemical structure: (R)-N-(3,4-difluoro-2-(2-fluoro-4-iodophenylamino)-6-methoxyphenyl)-1-(2,3-dihydroxypropyl)cyclopropane-1-sulfonamide] | B |

Example 9

XRPD Data

Figure 3:
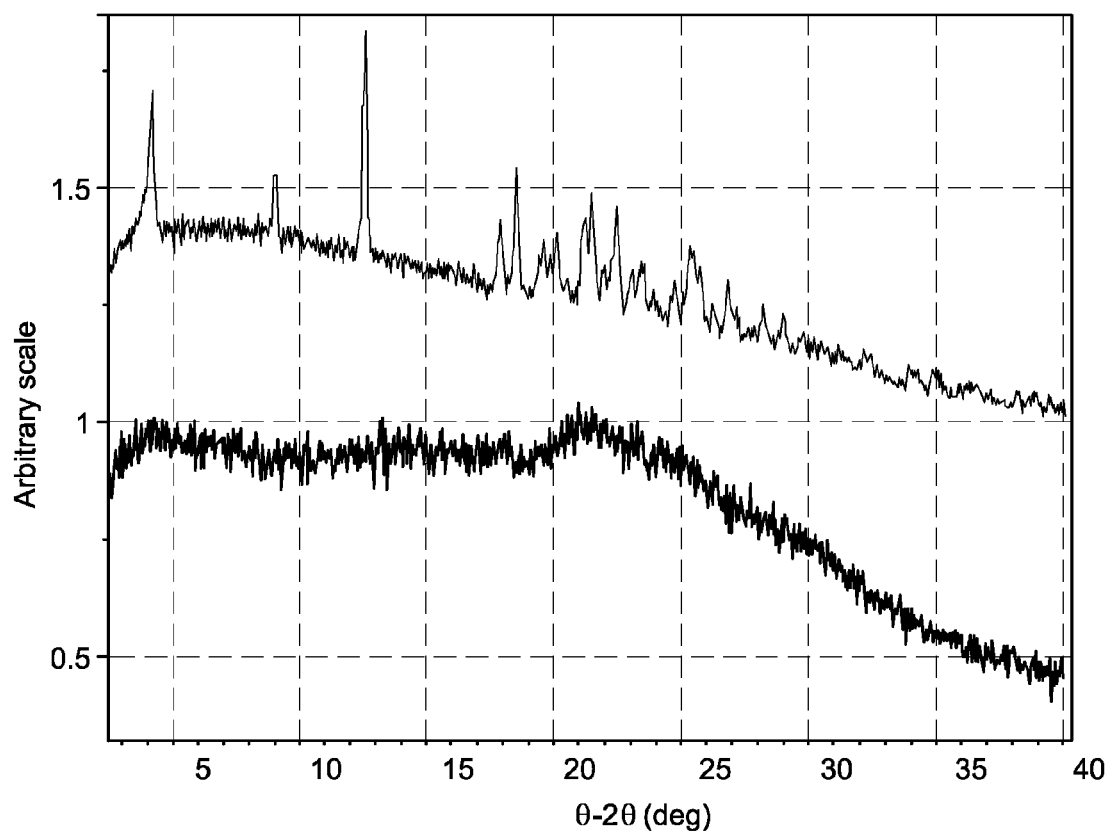
FIG. 3 is a graph of the PXRD patterns of N—(S)-(3,4-difluoro-2-(2-fluoro-4-iodophenylamino)-6-methoxyphenyl)-1-(2,3-dihydroxypropyl)cyclopropane-1-sulfonamide Form A (top) and N—(S)-(3,4-difluoro-2-(2-fluoro-4-iodophenylamino)-6-methoxyphenyl)-1-(2,3-dihydroxypropyl)cyclopropane-1-sulfonamide amorphous (bottom), generated using a Inel XRG-3000 diffractometer. The graph plots the intensity of the peaks as defined by counts per second versus the diffraction angle 2θ in degrees.

XPRD was performed on a Inel XRG-3000 diffractometer, equipped with a curved position-sensitive detector with a 2θ range of 120°. Real time data was collected using Cu Kα radiation at a resolution of 0.03 °2θ. The tube voltage and amperage were set to 40 kV and 30 mA, respectively. Patterns are displayed from 2.5 to 40 °2θ to facilitate direct pattern comparisons. Samples of (S)—N-(3,4-difluoro-2-(2-fluoro-4-iodophenylamino)-6-methoxyphenyl)-1-(2,3-dihydroxypropyl)cyclopropane-1-sulfonamide (synthesized as described herein) were prepared for analysis by packing them into thin-walled glass capillaries. Each capillary was moved onto a goniometer head that is motorized to permit spinning of the capillary during data acquisition. The samples were analyzed for 5 minutes. Instrument calibration was preformed daily using a silicon reference standard. FIG. 1 is a graph of a powder x-ray diffraction (PXRD) pattern of N—(S)-(3,4-difluoro-2-(2-fluoro-4-iodophenylamino)-6-methoxyphenyl)-1-(2,3-dihydroxypropyl)cyclopropane-1-sulfonamide Form A. FIG. 3 is a graph of the powder x-ray diffraction (PXRD) patterns of N—(S)-(3,4-difluoro-2-(2-fluoro-4-iodophenylamino)-6-methoxyphenyl)-1-(2,3-dihydroxypropyl)cyclopropane-1-sulfonamide Form A (top) and Amorphous (bottom).

Example 10

Differential Scanning Calorimetry (DSC)

Analyses were carried out on a TA Instruments differential scanning calorimeter Q1000. The instrument was calibrated using indium as the reference material. The sample was placed into a standard aluminum DSC pan with a non-crimped lid configuration, and the weight accurately recorded. To determine the glass transition temperature ($T_g$) of amorphous material, the sample cell was cycled several times between −40° C. and 140° C. The final temperature was ramped to 150° C. The $T_g$ is reported from the inflection point of the last cycle transition. FIG. 2 is a graph of a modulated DSC thermogram of N—(S)-(3,4-difluoro-2-(2-fluoro-4-iodophenylamino)-6-methoxyphenyl)-1-(2,3-dihydroxypropyl)cyclopropane-1-sulfonamide (Form A). The graph plots the normalized heat flow in Watts/gram (W/g) versus the measured sample temperature in ° C.

Example 11

Dynamic Vapor Sorption/Desorption (DVS)

Figure 4:
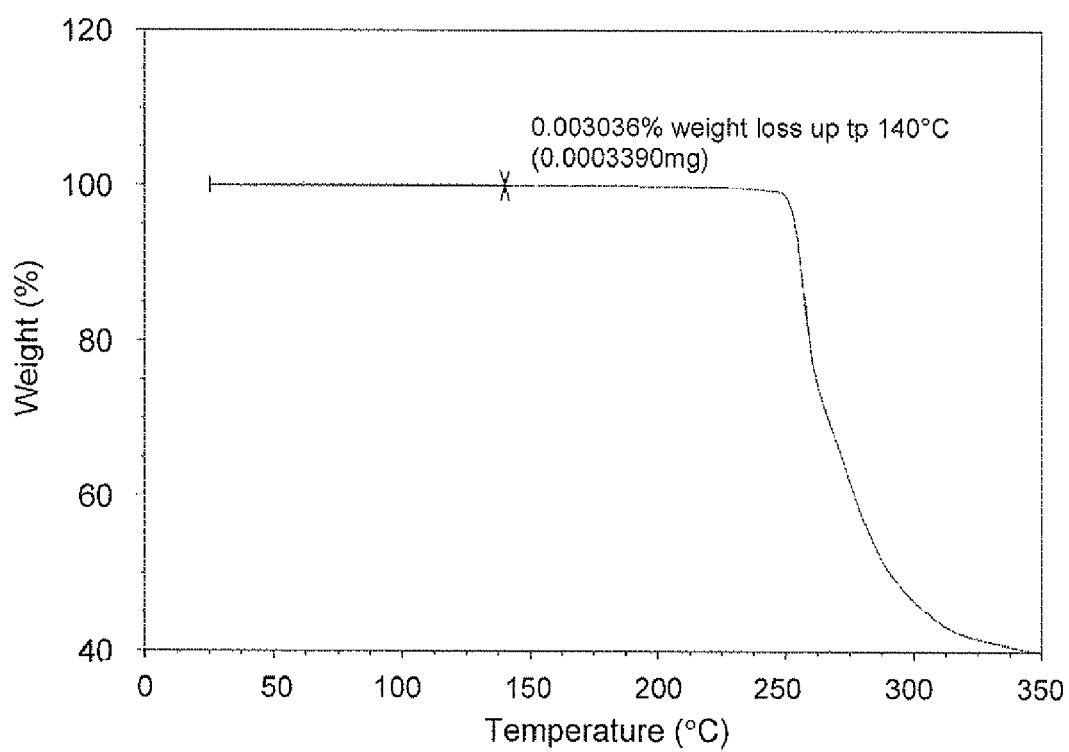
FIG. 4 shows a Dynamic Vapor Sorption/Desorption (DVS) isotherm of N—(S)-(3,4-difluoro-2-(2-fluoro-4-iodophenylamino)-6-methoxyphenyl)-1-(2,3-dihydroxypropyl)cyclopropane-1-sulfonamide Form A generated using a VTI SGA-100 Vapor Sorption Analyzer.

Moisture sorption/desorption data were collected on a VTI SGA-100 Vapor Sorption Analyzer. Sorption and desorption data were collected over a range of 5% to 95% relative humidity (RH) at 10% RH intervals under a nitrogen purge. Samples were not dried prior to analysis. Equilibrium criteria used for analysis were less than 0.0100% weight change in 5 minutes, with a maximum equilibration time of 3 hours if the weight criterion was not met. Data were not corrected for the initial moisture content of the samples. Sodium chloride and polyvinypyrrolidine were used as calibration standards. FIG. 4 shows a DVS isotherm of N—(S)-(3,4-difluoro-2-(2-fluoro-4-iodophenylamino)-6-methoxyphenyl)-1-(2,3-dihydroxypropyl)cyclopropane-1-sulfonamide (Form A). The material exhibits a negligible weight change during the experiment.

Example 12

Thermogravimetry (TG)

Figure 5:
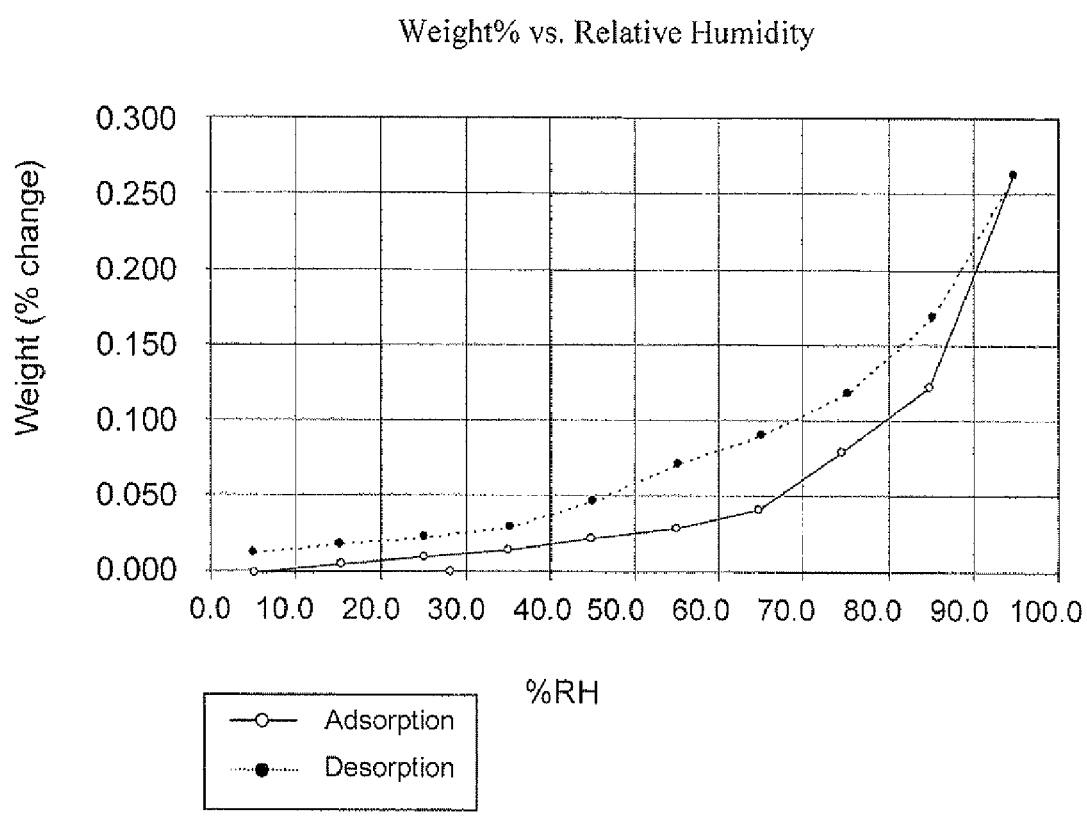
FIG. 5 shows a Thermogravimetry (TG) thermogram of N—(S)-(3,4-difluoro-2-(2-fluoro-4-iodophenylamino)-6-methoxyphenyl)-1-(2,3-dihydroxypropyl)cyclopropane-1-sulfonamide Form A) generated using a TA Instrument 2950 thermogravimetric analyzer.

Analyses were carried out on a TA Instrument 2950 thermogravimetric analyzer. The calibration standards were nickel and Alumel™. Each sample was placed in an aluminum sample pan and inserted into the TG furnace. Samples were equilibrated at 25° C., and then heated under a stream of nitrogen at a heating rate of 10° C./min, up to a final temperature of 350° C. FIG. 5 shows a TG thermogram of N—(S)-(3,4-difluoro-2-(2-fluoro-4-iodophenylamino)-6-methoxyphenyl)-1-(2,3-dihydroxypropyl)cyclopropane-1-sulfonamide (Form A) demonstrating negligible weight loss up to 140° C., indicating polymorph, form A is unsolvated.

What is claimed is:

1. A method of treating a MEK mediated disorder, wherein prevention is excluded, comprising administering to an individual in need thereof a therapeutically-effective amount of a crystalline polymorph of N—(S)-(3,4-difluoro-2-(2-fluoro-4-iodophenylamino)-6-methoxyphenyl)-1-(2,3-dihydroxypropyl)cyclopropane-1-sulfonamide having at least one of the following properties:
    (a) a powder x-ray diffraction pattern substantially the same as the powder x-ray diffraction pattern shown in FIG. 1 for said crystalline polymorph
    (b) a differential scanning calorimetry pattern substantially the same as the a differential scanning calorimetry pattern shown in FIG. 2 for said crystalline polymorph
    or
    (c) a melting point onset as determined by differential scanning calorimetry at about 143° C. for said crystalline polymorph.

2. A method of treating a MEK mediated disorder, wherein prevention is excluded, comprising administering to an individual in need thereof a therapeutically-effective amount of a crystalline polymorph of N-(3,4-difluoro-2-(2-fluoro-4-iodophenylamino)-6-methoxyphenyl)-1-(2,3-dihydroxypropyl)cyclopropane-1-sulfonamide made by a method comprising crystallizing amorphous N-(3,4-difluoro-2-(2-fluoro-4-iodophenylamino)-6-methoxyphenyl)-1-(2,3-dihydroxypropyl)cyclopropane-1-sulfonamide from a mixture of ethyl acetate and heptane to obtain said crystalline polymorph.

3. The method of claim 2, wherein the mixture of ethyl acetate and heptane is in a ratio of about 1-4 parts ethyl acetate to about 2-10 parts heptane.

4. The method of claim 2, wherein the mixture of ethyl acetate and heptane is in a ratio of about 2 parts ethyl acetate to about 5 parts heptane.

5. A method of treating a MEK mediated disorder, wherein prevention is excluded, comprising administering to an individual in need thereof a therapeutically-effective amount of a crystalline polymorph of N—(S)-(3,4-difluoro-2-(2-fluoro-4-iodophenylamino)-6-methoxyphenyl)-1-(2,3-dihydroxypropyl)cyclopropane-1-sulfonamide having at least one of the following properties:
(a) a powder x-ray diffraction pattern corresponding to the powder x-ray diffraction pattern shown in FIG. 1 for said crystalline polymorph
(b) a differential scanning calorimetry pattern corresponding to the differential scanning calorimetry pattern shown in FIG. 2 for said crystalline polymorph
or
(c) a melting point onset as determined by differential scanning calorimetry at about 143° C. for said crystalline polymorph.

6. The method of claim 5, wherein the crystalline polymorph of N—(S)-(3,4-difluoro-2-(2-fluoro-4-iodophenylamino)-6-methoxyphenyl)-1-(2,3-dihydroxypropyl)cyclopropane-1-sulfonamide has at least two of the following properties:
(a) a powder x-ray diffraction pattern corresponding to the powder x-ray diffraction pattern shown in FIG. 1 for said crystalline polymorph
(b) a differential scanning calorimetry pattern corresponding to the differential scanning calorimetry pattern shown in FIG. 2 for said crystalline polymorph
or
(c) a melting point onset as determined by differential scanning calorimetry at about 143° C. for said crystalline polymorph.

7. The method of claim 5, wherein the crystalline polymorph of N—(S)-(3,4-difluoro-2-(2-fluoro-4-iodophenylamino)-6-methoxyphenyl)-1-(2,3-dihydroxypropyl)cyclopropane-1-sulfonamide has the following properties:
(a) a powder x-ray diffraction pattern corresponding to the powder x-ray diffraction pattern shown in FIG. 1 for said crystalline polymorph
(b) a differential scanning calorimetry pattern corresponding to the differential scanning calorimetry pattern shown in the FIG. 2 for said crystalline polymorph
and
(c) a melting point onset as determined by differential scanning calorimetry at about 143° C. for said crystalline polymorph.

8. The method of claim 5, wherein the crystalline polymorph of N—(S)-(3,4-difluoro-2-(2-fluoro-4-iodophenylamino)-6-methoxyphenyl)-1-(2,3-dihydroxypropyl)cyclopropane-1-sulfonamide has a powder x-ray diffraction pattern corresponding to the powder x-ray diffraction pattern shown in FIG. 1 for said crystalline polymorph.

9. The method of claim 1, wherein the MEK mediated disorder is a cytokine-mediated disorder.

10. The method of claim 1, wherein the MEK mediated disorder is selected from the group consisting of immune disorders, inflammatory disorders, infectious disorders, proliferative disorders, and combinations thereof.

11. The method of claim 1, wherein the MEK mediated disorder is a cancer.

12. The method of claim 1, wherein the MEK mediated disorder is a fibrogenic disorder.

13. The method of claim 1, further comprising co-administering a second active agent.

14. The method of claim 1, further comprising co-administering a cytotoxic agent, an anti-angiogenesis agent, an anti-neoplastic agent, or a combination thereof.

15. The method of claim 1, further comprising surgery and/or radiation therapy.

16. The method of claim 2, wherein the MEK mediated disorder is a cytokine-mediated disorder.

17. The method of claim 2, wherein the MEK mediated disorder is selected from the group consisting of immune disorders, inflammatory disorders, infectious disorders, proliferative disorders, and combinations thereof.

18. The method of claim 2, wherein the MEK mediated disorder is a cancer.

19. The method of claim 2, wherein the MEK mediated disorder is a fibrogenic disorder.

20. The method of claim 2, further comprising co-administering a cytotoxic agent, an anti-angiogenesis agent, an anti-neoplastic agent, or a combination thereof and/or further comprising surgery and/or radiation therapy.

* * * * *